US012594270B2

(12) United States Patent
Granger et al.

(10) Patent No.: US 12,594,270 B2
(45) Date of Patent: Apr. 7, 2026

(54) SCHIZOPHRENIC DISORDER TREATMENT USING COMBINATION THERAPY

(71) Applicant: Cambridge Cognition Limited, Bottisham (GB)

(72) Inventors: Kiri Granger, Kilby (GB); Jennifer Barnett, Burwell (GB)

(73) Assignee: Cambridge Cognition Limited, Cambridge (GB)

( * ) Notice: Subject to any disclaimer, the term of this patent is extended or adjusted under 35 U.S.C. 154(b) by 885 days.

(21) Appl. No.: 17/755,084

(22) PCT Filed: Oct. 21, 2020

(86) PCT No.: PCT/EP2020/079651
§ 371 (c)(1),
(2) Date: Apr. 20, 2022

(87) PCT Pub. No.: WO2021/078810
PCT Pub. Date: Apr. 29, 2021

(65) Prior Publication Data
US 2022/0347166 A1 Nov. 3, 2022

Related U.S. Application Data

(60) Provisional application No. 62/924,114, filed on Oct. 21, 2019.

(51) Int. Cl.
| | |
|---|---|
| *A61K 31/465* | (2006.01) |
| *A61K 31/55* | (2006.01) |
| *A61K 45/06* | (2006.01) |
| *A61P 25/18* | (2006.01) |

(52) U.S. Cl.
CPC ............ *A61K 31/465* (2013.01); *A61K 31/55* (2013.01); *A61K 45/06* (2013.01); *A61P 25/18* (2018.01)

(58) Field of Classification Search
CPC ....... A61P 25/18; A61K 31/46; A61K 31/465; A61K 31/55; A61K 45/06
See application file for complete search history.

(56) References Cited

U.S. PATENT DOCUMENTS

| | | | |
|---|---|---|---|
| 9,937,163 B2 | 4/2018 | Hashimoto et al. | |
| 2013/0324572 A1 | 12/2013 | Hashimoto et al. | |

FOREIGN PATENT DOCUMENTS

| | | |
|---|---|---|
| WO | 2011133858 A2 | 10/2011 |
| WO | WO 2012/113850 A2 | 8/2012 |

OTHER PUBLICATIONS

Wallace et al. Expert Opinion Therapeutic Targets (2013) 17(2):139-155. (Year: 2013).*

Boggs, et al., Going up in Smoke? A Review of nAChRs-based Treatment Strategies for Improving Cognition in Schizophrenia, Curr Pharm Des.; 20(31): 5077-5092. (2014).

Dineley, et al., Nicotinic ACh Receptors as Therapeutic Targets in CNS Disorders, Trends Pharmacol Sci. Feb. 2015 ; 36(2): 96-108 (2014).

Ellenbroek, et al., Can 5-HT3 antagonists contribute toward the treatment of schizophrenia?, Behavioural Pharmacology, vol. 26 No 1&2, pp. 33-44 (2015).

Hashimoto, Development of new therapeutic drugs based on the pathophysiology of schizophrenia, Psychiatria et neurologia Japonica 113(4): 368-373 (2011).

Potasiewicz, Agnieszka, et al., Precognitive effects of varenicline in the animal model of schizophrenia depend on [alpha]4[beta]2- and [alpha]7-nicotinic acetylcholine receptors, Journal of Psychopharmacology., vol. 1, 33, No. 1, pp. 62-73 (2019).

Rahimian, Reza , et al., Tropisetron ameliorates ischemic brain injury in an embolic model of stroke, Brain Research, Elsevier, Amsterdam, NL, vol. 1392, pp. 101-109 (2011).

Rowe, et al., Dementia praecox redux: A systematic review of the nicotinic receptor as a target for cognitive symptoms of schizophrenia, Journal of Psychopharmacology, vol. 29(2) 197-211 (2015).

Shimizu, et al., Improving the Treatment of Schizophrenia: Role of 5-HT Receptors in Modulating Cognitive and Extrapyramidal Motor Functions, Laboratory of Pharmacology, CNS & Neurological Disorders—Drug Targets, vol. 12, No. 6 (2013).

Thompson, et al., Expert Opin Ther Targets. Author manuscript, PMC (Oct. 1, 2007).

WIPO, PCT Form ISA210, International Search Report for IA Patent Application Serial No. PCT/EP2020/079651, pp. 6 (mailed Jan. 20, 2021).

WIPO, PCT Form ISA237, Written Opinion for International Patent Application Serial No. PCT/EP2020/079651, pp. 9 (Jan. 20, 2021).

Zhang, et al., Short-Term Tropisetron Treatment and Cognitive and P50 Auditory Gating Deficits in Schizophrenia, The American journal of psychiatry, pp. 974-981 (Sep. 1, 2012).

Moran, et al., "IUPHAR review: Moving beyond dopamine-based therapeutic strategies for schizophrenia," *Pharmacological Research* 216:107727, May 2025, 26 pages.

Newhouse, et al., "Effects of nicotinic stimulation on cognitive performance," *Current Opinion in Pharmacology*, 4(1): pp. 36-46, Feb. 2004.

Declaration of Kiri Granger dated Dec. 1, 2025 and Valderrama-Lizarraga, et al., "Investigation of varenicline and tropisetron in latent inhibition and novel object recognition in mice," unpublished manuscript, 44 pages.

* cited by examiner

*Primary Examiner* — Kara R. Mcmillian

(74) *Attorney, Agent, or Firm* — Klarquist Sparkman, LLP

(57) ABSTRACT

The present specification disclose a combined therapy comprising one or more activators of an alpha-7 nicotinic acetylcholine receptor activity having 5-HT$_3$ receptor inhibitory activity and one or more activators of 5-HT$_3$ receptor activity for use in treating a schizophrenic disorder as well as methods of treating a schizophrenic disorder by administering a combined therapy comprising one or more activators of an alpha-7 nicotinic acetylcholine receptor activity having 5-HT$_3$ receptor inhibitory activity and one or more activators of 5-HT$_3$ receptor activity.

21 Claims, No Drawings

SCHIZOPHRENIC DISORDER TREATMENT USING COMBINATION THERAPY

This application is a 35 U.S.C. § 371 U.S. national stage patent application which claims the benefit of priority and is entitled to the filing date of International Patent Application PCT/EP2020/079651, filed Oct. 21, 2020, an international patent application which claims the benefit of priority and is entitled to the filing date pursuant of 35 U.S.C. § 119(e) of U.S. Provisional Patent Application 62/924,114, filed Oct. 21, 2019, the content of each of which is hereby incorporated by reference in its entirety.

A schizophrenic disorder is generally considered to be a syndrome, probably a group of mental disorders, involving a breakdown in the relation between thought, emotion, and behavior leading to diverse disturbances in cognition, perception, reality testing, actions, feelings, mood, interpersonal relations, social interaction, and occupational function. A chronic, severe, and disabling psychiatric disorder, a schizophrenic disorder affects 0.5% to 1% of the global population. Both men and women are at equal risk in developing this brain disorder, which occurs at similar rates in all ethnic groups around the world. Disease onset shows a gender-bias with men usually showing symptoms between their late teens and early twenties and women usually develop symptoms during their mid-twenties to early thirties.

A schizophrenic disorder affects people differently and symptoms can vary from person to person. Some people can have many symptoms, while others may only have a few. The clinical features of a schizophrenic disorder can be clustered into three symptom groups, positive symptoms, negative symptom and cognitive symptoms. Positive symptoms are classified as fixed, false feelings or behaviors involving real-life situations that could be true but are simply manifestations of psychosis, such as, e.g., delusions, hallucinations, paranoia, thought disorders (disorganized thinking, speech or behavior, neologism) and movement disorders (clumsy, uncoordinated, repetitious movements, catatonia). Negative symptoms are classified as deficits or reductions in normal emotion and behavior, such as, e.g., affective disturbances (immobile expression, monotonous voice), reduced interest or lack of pleasure in everyday activities (anhedonia, like depression), lack of motivation (avolition), decreased ability to initiate and sustain planned activity, poverty of speech (alogia), infrequent speech (even when forced to interact), and social withdrawal. Cognitive symptoms are classified as deficits in the mental processes of comprehension, judgement, memory and reasoning, such as, e.g., problems in selective attention, working memory, executive function, episodic memory, language comprehension and social-emotional processing. The disease is also associated with some quantitative abnormalities in brain structure, e.g., enlarged ventricles and decreased temporal lobe volume, but these abnormalities are not specific to a schizophrenic disorder. While the emergence of positive symptoms in early adulthood is the most striking clinical feature, cognitive deficits are a core feature of the disorder, are present prior to the onset of psychosis and are the single best predictor of long-term functional outcome.

There is currently no cure for a schizophrenic disorder and individuals diagnosed with this mental illness require chronic treatment. The primary treatment of a schizophrenic disorder is antipsychotic medications, often in combination with psychological and social supports. Clinical studies have shown that early treatment using antipsychotic drugs can be effective in managing symptoms of psychosis before serious complications develop and in improving the long-term outlook of such treated individuals. For this reason, antipsychotic drug treatment is considered a key component of a schizophrenic disorder treatment and is recommended by the National Institute of Health and Care Excellence (NICE), the American Psychiatric Association, and the British Society for Psychopharmacology.

Currently, all approved antipsychotic drugs work relatively the same way, by antagonizing D2 dopamine receptors. Unfortunately, dopaminergic-based antipsychotic drugs are effective only in managing the positive symptoms of a schizophrenic disorder. Such medications have little to no effect on negative or cognitive symptoms, which are the most disabling impairments to an individual in leading a normal life, and that most affect their quality of living. The ineffectiveness of dopaminergic-based antipsychotic drugs is a driving factor for the poor social and functional outcomes that bring high personal and societal costs to an individual suffering from a schizophrenic disorder. Despite considerable recent effort by the pharmaceutical industry, no novel mechanisms have yet been approved for addressing the cognitive and negative symptoms associated with a schizophrenic disorder and there have been many late-stage failures. It is, therefore, of paramount importance to identify new therapeutic approaches for the treatment of a schizophrenic disorder.

The present specification discloses a combination therapy comprising an alpha-7 nicotinic acetylcholine receptor agonist having 5-HT$_3$ receptor inhibitory activity and a serotonin agonist useful in the effective treatment of a schizophrenic disorder. A disclosed serotonin agonist may optionally further include an alpha-7 nicotinic acetylcholine receptor agonistic activity. Such combination therapy successfully mitigates gastrointestinal side effects to facilitate and enable long-term treatment that effectively ameliorates positive, negative and cognitive symptoms of this mental illness.

SUMMARY

Aspects of the present specification disclose methods of treating a schizophrenic disorder by administering a combined therapy comprising one or more activators of an alpha-7 nicotinic acetylcholine receptor activity having 5-HT$_3$ receptor inhibitory activity and one or more activators of 5-HT$_3$ receptor activity.

Aspects of the present specification disclose a combined therapy for use in treating a schizophrenic disorder, the combined therapy comprising one or more activators of an alpha-7 nicotinic acetylcholine receptor activity having 5-HT$_3$ receptor inhibitory activity and one or more activators of 5-HT$_3$ receptor activity.

Aspects of the present specification disclose use of a combined therapy in treating a schizophrenic disorder, the combined therapy comprising one or more activators of an alpha-7 nicotinic acetylcholine receptor activity having 5-HT$_3$ receptor inhibitory activity and one or more activators of 5-HT$_3$ receptor activity.

Aspects of the present specification disclose use of one or more activators of an alpha-7 nicotinic acetylcholine receptor activity having 5-HT$_3$ receptor inhibitory activity and one or more activators of 5-HT$_3$ receptor activity in the manufacture of a medicament for treating a schizophrenic disorder.

Aspects of the present specification disclose methods of treating a schizophrenic disorder by administering a combined therapy comprising one or more alpha-7 nicotinic acetylcholine receptor agonist having 5-HT$_3$ receptor antagonistic activity and one or more 5-HT$_3$ receptor agonists.

Aspects of the present specification disclose a combined therapy for use in treating a schizophrenic disorder, the combined therapy comprising one or more alpha-7 nicotinic acetylcholine receptor agonist having 5-HT$_3$ receptor antagonistic activity and one or more 5-HT$_3$ receptor agonists.

Aspects of the present specification disclose use of a combined therapy in treating a schizophrenic disorder, the combined therapy comprising one or more alpha-7 nicotinic acetylcholine receptor agonist having 5-HT$_3$ receptor antagonistic activity and one or more activators of 5-HT$_3$ receptor activity.

Aspects of the present specification disclose use of one or more alpha-7 nicotinic acetylcholine receptor agonist having 5-HT$_3$ receptor antagonistic activity and one or more activators of 5-HT$_3$ receptor activity in the manufacture of a medicament for treating a schizophrenic disorder.

Aspects of the present specification disclose methods of treating a schizophrenic disorder by administering a combined therapy comprising one or more alpha-7 nicotinic acetylcholine receptor agonist having 5-HT$_3$ receptor inverse agonistic activity and one or more 5-HT$_3$ receptor agonists.

Aspects of the present specification disclose a combined therapy for use in treating a schizophrenic disorder, the combined therapy comprising one or more alpha-7 nicotinic acetylcholine receptor agonist having 5-HT$_3$ receptor inverse agonistic activity and one or more 5-HT$_3$ receptor agonists.

Aspects of the present specification disclose use of a combined therapy in treating a schizophrenic disorder, the combined therapy comprising one or more alpha-7 nicotinic acetylcholine receptor agonist having 5-HT$_3$ receptor inverse agonistic activity and one or more activators of 5-HT$_3$ receptor activity.

Aspects of the present specification disclose use of one or more alpha-7 nicotinic acetylcholine receptor agonist having 5-HT$_3$ receptor inverse agonistic activity and one or more activators of 5-HT$_3$ receptor activity in the manufacture of a medicament for treating a schizophrenic disorder.

DETAILED DESCRIPTION

As with all family members, the alpha-7 nicotinic acetylcholine receptor ($\alpha$7 nAChR) is considered a cholinergic receptor because it responds to the neurotransmitter acetylcholine. $\alpha$7 nAChR are pentameric polypeptides consisting entirely of $\alpha$7 subunits [i.e., $(\alpha 7)_5$ stoichiometry]. Located in the brain, $\alpha$7 nAChR appear to be critical for memory, working memory, learning, and attention.

Agonists of the $\alpha$7 nAChR were developed as potential therapeutic for use in alleviating the cognitive impairment associated with schizophrenia due to their positive effects on neurocognition. However, to date all such drug candidates have failed during clinical trials, typically at phase 2 or 3 (e.g., Abbvie, Forum Pharmaceuticals, Roche). Although the safety profile of these $\alpha$7 nAChR agonists was generally good, one adverse outcome associated with their use was gastrointestinal (GI) side effects including a reduction in gut transit and constipation driven by the 5-HT3 receptor antagonistic activity of these $\alpha$7 nAChR agonists.

5-hydroxytryptamine (5-HT) or serotonin is a monoamine neurotransmitter that mediates an individual's perceptions of resources, having have diverse effects on mood, anxiety, sleep, appetite, temperature, eating behavior, sexual behavior, movements, and gastrointestinal motility. This neurotransmitter is produced primarily in the enteric nervous system located in the gastrointestinal tract but is also found in the central nervous system (CNS), specifically in the Raphe nuclei located in the brainstem.

Serotonin mediates its action through serotonin receptors (5-HT receptors). Upon binding of its ligand, serotine receptors modulate the release of many neurotransmitters, including glutamate, GABA, dopamine, epinephrine/norepinephrine, and acetylcholine, as well as many hormones, including oxytocin, prolactin, vasopressin, cortisol, corticotropin, and substance P. Mediating both excitatory and inhibitory neurotransmission, serotonin receptors influence various biological and neurological processes such as aggression, anxiety, appetite, cognition, learning, memory, mood, nausea, sleep, and thermoregulation. Divided into seven families, serotonin receptors are found in the central and peripheral nervous systems.

Except for the serotonin type 3 (5-HT$_3$) receptor, all other 5-HT receptors are G-protein-coupled receptors that activate an intracellular second messenger cascade.

The 5-HT$_3$ receptor belongs to the Cys-loop superfamily of ligand-gated ion channels (LGICs) that includes receptors for acetylcholine, $\gamma$-aminobutyric acid-type-A (GABA)$_A$ and glycine and therefore differs structurally and functionally from all other 5-HT receptors. This ion channel is cation-selective and mediates rapid neuronal depolarization and excitation predominantly carried by an inward current of sodium and/or potassium ions. The 5-HT$_3$ receptor is found many regions of the CNS including the entorhinal cortex, hippocampus CA1 area, amygdala, substantia nigra, and brainstem, and the peripheral nervous systems and mediates a variety of physiological functions. On a cellular level, it has been shown that postsynaptic 5-HT$_3$ receptors mediate fast excitatory synaptic transmission in neocortical interneurons, amygdala, and hippocampus, and in the visual cortex. 5-HT$_3$ receptors are also present on presynaptic nerve terminals. The 5-HT$_3$ receptors also play an important role in the enteric nervous system.

As with other ligand gated ion channels, the functional 5-HT$_3$ receptor forms a pentamer of five pseudo-symmetrically arranged subunits surrounding a central ion conducting pore. Currently five 5-HT$_3$ receptor subunits are known (5-HT$_{3A}$ to 5-HT$_{3E}$). A functional channel may be composed of five identical 5-HT$_{3A}$ subunits (homopentameric) or a mixture of 5-HT$_{3A}$ and one of the other four 5-HT$_{3B}$, 5-HT$_{3C}$, 5-HT$_{3D}$, or 5-HT$_{3E}$ subunits (heteropentameric). Each subunit comprises an extracellular N-terminal domain which comprises the orthosteric ligand-binding site; a transmembrane domain consisting of four interconnected alpha helices (M1-M4), with the extracellular M2-M3 loop involved in the gating mechanism; a large cytoplasmic domain between M3 and M4 involved in receptor trafficking and regulation; and a short extracellular C-terminus. Whereas extracellular domain is the site of action of agonists and competitive antagonists, the transmembrane domain contains the central ion pore, receptor gate, and principle selectivity filter that allows ions to cross the cell membrane.

Besides its endogenous ligand serotonin, the downstream activities mediated by 5-HT$_3$ receptors can be modulated by exogenous compounds such as, e.g., a 5-HT$_3$ receptor agonist, a 5-HT$_3$ receptor antagonist or a 5-HT$_3$ receptor inverse agonist. 5-HT$_3$ receptor agonists and inverse agonists do not appear to be of any clinical interests, being used primarily as preclinical reagents. On the other hand, 5-HT$_3$ receptor antagonists are potent antiemetics used for prevention of postsurgical or chemotherapy induced nausea and vomiting and for some agents as therapy of diarrhea-predominant irritable bowel syndrome. The antiemetic effects appear to be the result of both central and peripheral inhibition of serotonin activity, with a decrease in vagal activity as well as interruption of pathways in the chemoreceptor trigger zone and solitary tract nucleus of the brainstem.

The present specification discloses in part, methods of treating a schizophrenic disorder. In one embodiment, a method of treating a schizophrenic disorder disclosed herein comprises, consists essentially of, or consists of administering a combined therapy comprising, consisting essentially of, or consisting of one or more activators of an alpha-7 nicotinic acetylcholine receptor activity having 5-HT$_3$ receptor inhibitory activity and one or more activators of 5-HT$_3$ receptor activity. In one embodiment, a method of treating a schizophrenic disorder disclosed herein comprises, consists essentially of, or consists of administering a combined therapy comprising, consisting essentially of, or consisting of one or more alpha-7 nicotinic acetylcholine receptor agonists having 5-HT$_3$ receptor antagonistic activity and one or more 5-HT$_3$ receptor agonists. In one embodiment, a method of treating a schizophrenic disorder disclosed herein comprises, consists essentially of, or consists of administering a combined therapy comprising, consisting essentially of, or consisting of one or more alpha-7 nicotinic acetylcholine receptor agonists having 5-HT$_3$ receptor inverse agonistic activity and one or more 5-HT$_3$ receptor agonists. In a preferred embodiment, a method of treating a schizophrenic disorder disclosed herein comprises, consists essentially of, or consists of administering a combined therapy comprising, consisting essentially of, or consisting of Tropisetron and Varenicline. In the embodiments disclosed above, an amount of an activators of an alpha-7 nicotinic acetylcholine receptor activity having 5-HT$_3$ receptor inhibitory activity, an activator of 5-HT$_3$ receptor activity, an alpha-7 nicotinic acetylcholine receptor agonist having 5-HT$_3$ receptor antagonistic activity, an alpha-7 nicotinic acetylcholine receptor agonist having 5-HT$_3$ receptor inverse agonistic activity, a 5-HT$_3$ receptor agonist, Varenicline and/or Tropisetron is a therapeutically effective amount.

The present specification discloses, in part, a combined therapy for use in treating a schizophrenic disorder. In one embodiment, a combined therapy comprising, consists essentially of, or consists of one or more activators of an alpha-7 nicotinic acetylcholine receptor activity having 5-HT$_3$ receptor inhibitory activity and one or more activators of 5-HT$_3$ receptor activity for use in treating a schizophrenic disorder. In one embodiment, a combined therapy comprising, consists essentially of, or consists of one or more alpha-7 nicotinic acetylcholine receptor agonists having 5-HT$_3$ receptor antagonistic activity and one or more 5-HT$_3$ receptor agonists for use in treating a schizophrenic disorder. In one embodiment, a combined therapy comprising, consists essentially of, or consists of one or more alpha-7 nicotinic acetylcholine receptor agonists having 5-HT$_3$ receptor inverse agonistic activity and one or more 5-HT$_3$ receptor agonists for use in treating a schizophrenic disorder. In a preferred embodiment, a combined therapy comprising, consists essentially of, or consists of Tropisetron and Varenicline for use in treating a schizophrenic disorder. In the embodiments disclosed above, an amount of an activators of an alpha-7 nicotinic acetylcholine receptor activity having 5-HT$_3$ receptor inhibitory activity, an activator of 5-HT$_3$ receptor activity, an alpha-7 nicotinic acetylcholine receptor agonist having 5-HT$_3$ receptor antagonistic activity, an alpha-7 nicotinic acetylcholine receptor agonist having 5-HT$_3$ receptor inverse agonistic activity, a 5-HT$_3$ receptor agonist, Varenicline and/or Tropisetron is a therapeutically effective amount.

The present specification discloses, in part, a combination therapy. A combination therapy encompasses separate use or administration of a first composition comprising, consists essentially of, or consists of one or more activators of 5-HT$_3$ receptor activity and a second composition comprising, consists essentially of, or consists of one or more activators of an alpha-7 nicotinic acetylcholine receptor activity having 5-HT$_3$ receptor inhibitory activity or a use or administration of a single composition comprising, consists essentially of, or consists of one or more activators of 5-HT$_3$ receptor activity and one or more activators of an alpha-7 nicotinic acetylcholine receptor activity having 5-HT$_3$ receptor inhibitory activity. In an aspect of this embodiment, a combination therapy encompasses separate use or administration of a first composition comprising, consists essentially of, or consists of one or more 5-HT$_3$ receptor agonists and a second composition comprising, consists essentially of, or consists of one or more alpha-7 nicotinic acetylcholine receptor agonists having 5-HT$_3$ receptor antagonistic activity or a use or administration of a single composition comprising, consists essentially of, or consists of one or more 5-HT$_3$ receptor agonists and one or more alpha-7 nicotinic acetylcholine receptor agonists having 5-HT$_3$ receptor antagonistic activity. In another aspect of this embodiment, a combination therapy encompasses separate use or administration of a first composition comprising, consists essentially of, or consists of one or more 5-HT$_3$ receptor agonists and a second composition comprising, consists essentially of, or consists of one or more alpha-7 nicotinic acetylcholine receptor agonists having 5-HT$_3$ receptor inverse agonistic activity or a use or administration of a single composition comprising, consists essentially of, or consists of one or more 5-HT$_3$ receptor agonists and one or more alpha-7 nicotinic acetylcholine receptor agonists having 5-HT$_3$ receptor inverse agonistic activity. In a preferred embodiment, a combination therapy encompasses separate use or administration of a first composition comprising, consists essentially of, or consists of Varenicline and a second composition comprising Tropisetron or a use or administration of a single composition comprising, consists essentially of, or consists of Varenicline and Tropisetron. In the embodiments disclosed above, an amount of an inhibitor of 5-HT3 receptor activity, an activator of 5-HT$_3$ receptor activity, an alpha-7 nicotinic acetylcholine receptor agonist having 5-HT$_3$ receptor antagonistic activity, an alpha-7 nicotinic acetylcholine receptor agonist having 5-HT$_3$ receptor inverse agonistic activity, a 5-HT$_3$ receptor agonist, Varenicline and/or Tropisetron is a therapeutically effective amount. In all embodiments disclosed above, a first and second composition can be used or administered sequentially in any order or simultaneously.

In one embodiment, a combination therapy disclosed herein can comprise a single activator of 5-HT$_3$ receptor activity and a single activator of an alpha-7 nicotinic acetylcholine receptor activity having 5-HT$_3$ receptor inhibitory activity, a plurality of activators of 5-HT$_3$ receptor activity and a single activator of an alpha-7 nicotinic acetylcholine receptor activity having 5-HT$_3$ receptor inhibitory activity, a single activator of 5-HT$_3$ receptor activity and a plurality of activators of an alpha-7 nicotinic acetylcholine receptor activity having 5-HT$_3$ receptor inhibitory activity, or a plurality of activators of 5-HT$_3$ receptor activity and a plurality of activators of an alpha-7 nicotinic acetylcholine receptor activity having 5-HT$_3$ receptor inhibitory activity.

In aspects of this embodiment, a combination therapy can comprise 1-2, 1-3, 1-4, 1-5, 2-3, 2-4, 2-5, 3-4, 3-5, or 4-5 activators of 5-$HT_3$ receptor activity and a single activator of an alpha-7 nicotinic acetylcholine receptor activity having 5-$HT_3$ receptor inhibitory activity. In other aspects of this embodiment, a combination therapy can comprise a single activator of 5-$HT_3$ receptor activity and 1-2, 1-3, 1-4, 1-5, 2-3, 2-4, 2-5, 3-4, 3-5, or 4-5 activators of an alpha-7 nicotinic acetylcholine receptor activity having 5-$HT_3$ receptor inhibitory activity. In yet other aspects of this embodiment, a combination therapy can comprise 1-2, 1-3, 1-4, 1-5, 2-3, 2-4, 2-5, 3-4, 3-5, or 4-5 activators of 5-$HT_3$ receptor activity and 1-2, 1-3, 1-4, 1-5, 2-3, 2-4, 2-5, 3-4, 3-5, or 4-5 activators of an alpha-7 nicotinic acetylcholine receptor activity having 5-$HT_3$ receptor inhibitory activity.

In one embodiment, a combination therapy disclosed herein can comprise a single 5-$HT_3$ receptor agonist and a single alpha-7 nicotinic acetylcholine receptor agonist having 5-$HT_3$ receptor antagonistic activity, a plurality of 5-$HT_3$ receptor agonists and a single alpha-7 nicotinic acetylcholine receptor agonist having 5-$HT_3$ receptor antagonistic activity, a single 5-$HT_3$ receptor agonist and a plurality of alpha-7 nicotinic acetylcholine receptor agonists having 5-$HT_3$ receptor antagonistic activity, or a plurality of 5-$HT_3$ receptor agonists and a plurality of alpha-7 nicotinic acetylcholine receptor agonists having 5-$HT_3$ receptor antagonistic activity. In aspects of this embodiment, a combination therapy can comprise 1-2, 1-3, 1-4, 1-5, 2-3, 2-4, 2-5, 3-4, 3-5, or 4-5 5-$HT_3$ receptor agonists and a single alpha-7 nicotinic acetylcholine receptor agonist having 5-$HT_3$ receptor antagonistic activity. In other aspects of this embodiment, a combination therapy can comprise a single 5-$HT_3$ receptor agonist and 1-2, 1-3, 1-4, 1-5, 2-3, 2-4, 2-5, 3-4, 3-5, or 4-5 alpha-7 nicotinic acetylcholine receptor agonists having 5-$HT_3$ receptor antagonistic activity. In yet other aspects of this embodiment, a combination therapy can comprise 1-2, 1-3, 1-4, 1-5, 2-3, 2-4, 2-5, 3-4, 3-5, or 4-5 5-$HT_3$ receptor agonists and 1-2, 1-3, 1-4, 1-5, 2-3, 2-4, 2-5, 3-4, 3-5, or 4-5 alpha-7 nicotinic acetylcholine receptor agonists having 5-$HT_3$ receptor antagonistic activity.

In one embodiment, a combination therapy disclosed herein can comprise a single 5-$HT_3$ receptor agonist and a single alpha-7 nicotinic acetylcholine receptor agonist having 5-$HT_3$ receptor inverse agonistic activity, a plurality of 5-$HT_3$ receptor agonists and a single alpha-7 nicotinic acetylcholine receptor agonist having 5-$HT_3$ receptor inverse agonistic activity, a single 5-$HT_3$ receptor agonist and a plurality of alpha-7 nicotinic acetylcholine receptor agonists having 5-$HT_3$ receptor inverse agonistic activity, or a plurality of 5-$HT_3$ receptor agonists and a plurality of alpha-7 nicotinic acetylcholine receptor agonists having 5-$HT_3$ receptor inverse agonistic activity. In aspects of this embodiment, a combination therapy can comprise 1-2, 1-3, 1-4, 1-5, 2-3, 2-4, 2-5, 3-4, 3-5, or 4-5 5-$HT_3$ receptor agonists and a single alpha-7 nicotinic acetylcholine receptor agonist having 5-$HT_3$ receptor inverse agonistic activity. In other aspects of this embodiment, a combination therapy can comprise a single 5-$HT_3$ receptor agonist and 1-2, 1-3, 1-4, 1-5, 2-3, 2-4, 2-5, 3-4, 3-5, or 4-5 alpha-7 nicotinic acetylcholine receptor agonists having 5-$HT_3$ receptor inverse agonistic activity. In yet other aspects of this embodiment, a combination therapy can comprise 1-2, 1-3, 1-4, 1-5, 2-3, 2-4, 2-5, 3-4, 3-5, or 4-5 5-$HT_3$ receptor agonists and 1-2, 1-3, 1-4, 1-5, 2-3, 2-4, 2-5, 3-4, 3-5, or 4-5 alpha-7 nicotinic acetylcholine receptor agonists having 5-$HT_3$ receptor inverse agonistic activity.

The present specification discloses, in part, an activator of 5-$HT_3$ receptor activity. An activator of 5-$HT_3$ receptor activity is any molecule that initiates increases, enhances, or otherwise activates the activity of a 5-$HT_3$ receptor. Non-limiting examples of an activator of 5-$HT_3$ receptor activity include a 5-$HT_3$ receptor agonist.

The present specification discloses, in part, an activator of an alpha-7 nicotinic acetylcholine receptor activity having 5-$HT_3$ receptor inhibitory activity. An activator of an alpha-7 nicotinic acetylcholine receptor activity having 5-$HT_3$ receptor inhibitory activity is any molecule that initiates increases, enhances, or otherwise activates the activity of an alpha-7 nicotinic acetylcholine receptor that also reduces, dampens, prevents or otherwise inhibits the activity of a 5-$HT_3$ receptor. Non-limiting examples of an activator of an alpha-7 nicotinic acetylcholine receptor activity having 5-$HT_3$ receptor inhibitory activity include an alpha-7 nicotinic acetylcholine receptor agonist having 5-$HT_3$ receptor antagonistic activity and an alpha-7 nicotinic acetylcholine receptor agonist having 5-$HT_3$ receptor inverse agonistic activity.

The present specification discloses, in part, a 5-$HT_3$ receptor agonist. A 5-$HT_3$ receptor agonist is a compound that binds to a 5-$HT_3$ receptor and activates or provokes the receptor to produce a biological response. A 5-$HT_3$ receptor agonist disclosed herein can be a full agonist, a partial agonist, a co-agonist or a super-agonist. A 5-$HT_3$ full receptor agonist bind to and activate a 5-$HT_3$ receptor with the maximum response that an agonist can elicit at the receptor. A 5-$HT_3$ partial receptor agonist bind and activate a given 5-$HT_3$ receptor, but elicits only partial effect at the receptor relative to a full agonist, even at maximal receptor occupancy. Although they are agonists, 5-$HT_3$ receptor partial agonists can act as a competitive antagonist in the presence of a 5-$HT_3$ receptor full agonist, as it competes with the full agonist for receptor occupancy, thereby producing a net decrease in the receptor activation as compared to that observed with the full agonist alone A 5-$HT_3$ co-agonist works together with other 5-$HT_3$ receptor co-agonists to produce the desired biological response. A 5-$HT_3$ receptor agonist disclosed herein can be a 5-$HT_3$ receptor super-agonist which is capable of producing a greater biological response at that receptor than serotonin.

A 5-$HT_3$ receptor agonist disclosed herein can be a pan-agonist or a selective agonist. A 5-$HT_3$ receptor pan-agonist binds to and elicits a biological response from any 5-HT-3 receptor irrespective of subunit composition. A 5-$HT_3$ receptor selective agonist binds selective to a specific type of 5-$HT_3$ receptor, eliciting a biological response of via these specific 5-$HT_3$ receptors. For example, a 5-$HT_3$ selective agonist can bind to and elicit a biological response from only 5-$HT_3$ homopentameric receptors, or only 5-$HT_3$ heteropentameric receptors, or only 5-$HT_3$ heteropentameric receptors of certain subunit composition, such as, e.g., 5-$HT_{3AC}$ heteropentameric receptors, 5-$HT_{3AD}$ heteropentameric receptors, or 5-$HT_{3AE}$ heteropentameric receptors.

A 5-$HT_3$ receptor agonist disclosed herein includes, without limitation, an alcohol having 5-$HT_3$ receptor agonist activity, meta-Chlorophenylbiguanide (1-(3-Chlorophenyl-biguanide)), Ibogaine, Phenylbiguanide, a piperazine having 5-$HT_3$ receptor agonist activity, RS-56812 (N-(1-Azabicyclo[2.2.2]octan-3-yl)-2-(1-methylindol-3-yl)-2-oxoacet-amide), Serotonin (5-HT), SR-57227 (1-(6-Chloropyridin-2-yl)piperidin-4-amine), SR-57227A (4-Amino-1-(6-chloro-2-pyridyl)-piperidine hydrochloride), a tryptamine having 5-$HT_3$ receptor agonist activity, Varenicline, a volatile gas having 5-$HT_3$ receptor agonist activity, and YM-31636 (2-

(1H-imidazol-4-ylmethyl)-8H-indeno[1,2-d]thiazole). Non-limiting examples of an alcohol having 5-HT$_3$ receptor agonist activity include butanol, ethanol, and trichloroethanol. Non-limiting examples of a piperazine having 5-HT$_3$ receptor agonist activity include benzylpiperazine, meta-Chlorophenylpiperazine, and quipazine. Non-limiting examples of a tryptamine having 5-HT$_3$ receptor agonist activity include 2-methyl-5-hydroxytryptamine, $\alpha$-Methyltryptamine, 5-carboxamidotryptamine, N,N-Dimethyl-5-hydroxytryptamine (Bufotenin), and 5-hydroxy-N,N,N-trimethyltryptammonium (bufotenine). Non-limiting examples of a volatile gas having 5-HT$_3$ receptor agonist activity include halothane, isoflurane, toluene, and trichloroethane.

The present specification discloses, in part, an alpha-7 nicotinic acetylcholine receptor agonist. An alpha-7 nicotinic acetylcholine receptor agonist is a compound that binds to an alpha-7 nicotinic acetylcholine receptor and activates or provokes the receptor to produce a biological response. An alpha-7 nicotinic acetylcholine receptor agonist disclosed herein can be a full agonist, a partial agonist, a co-agonist or a super-agonist. An alpha-7 nicotinic acetylcholine full receptor agonist bind to and activate a alpha-7 nicotinic acetylcholine receptor with the maximum response that an agonist can elicit at the receptor. An alpha-7 nicotinic acetylcholine partial receptor agonist bind and activate a given alpha-7 nicotinic acetylcholine receptor, but elicits only partial effect at the receptor relative to a full agonist, even at maximal receptor occupancy. Although they are agonists, alpha-7 nicotinic acetylcholine receptor partial agonists can act as a competitive antagonist in the presence of a alpha-7 nicotinic acetylcholine receptor full agonist, as it competes with the full agonist for receptor occupancy, thereby producing a net decrease in the receptor activation as compared to that observed with the full agonist alone An alpha-7 nicotinic acetylcholine co-agonist works together with other alpha-7 nicotinic acetylcholine receptor co-agonists to produce the desired biological response. An alpha-7 nicotinic acetylcholine receptor agonist disclosed herein can be a alpha-7 nicotinic acetylcholine receptor super-agonist which is capable of producing a greater biological response at that receptor than serotonin.

An alpha-7 nicotinic acetylcholine receptor agonist disclosed herein can be a pan-agonist or a selective agonist. An alpha-7 nicotinic acetylcholine receptor pan-agonist binds to and elicits a biological response from any alpha-7 nicotinic acetylcholine receptor irrespective of subunit composition. An alpha-7 nicotinic acetylcholine receptor selective agonist binds selective to a specific type of alpha-7 nicotinic acetylcholine receptor, eliciting a biological response of via these specific alpha-7 nicotinic acetylcholine receptors. For example, a 5-HT$_3$ selective agonist can bind to and elicit a biological response from only $\alpha$7 nAChR homopentameric receptors or only $\alpha$7 nAChR heteropentameric receptors.

An alpha-7 nicotinic acetylcholine receptor agonist disclosed herein includes, without limitation, (+)-N-(1-azabicyclo[2.2.2]oct-3-yl)benzo[b]furan-2-carboxamide, A-582941, Acetylcholine, Amyloid beta, Anabasine, AR-R17779, Bradanicline, Choline, Encenicline, Epiboxidine, GTS-21, ICH-3, Nicotine, PHA-543,613, PHA-709829, PNU-282,987, SSR-180,711, TC-1698, Tilorone, Tropisetron, and WAY-317,538.

The present specification discloses, in part, an activator of an alpha-7 nicotinic acetylcholine receptor activity having 5-HT$_3$ receptor inhibitory activity. An activator of an alpha-7 nicotinic acetylcholine receptor activity having 5-HT$_3$ receptor inhibitory activity is an alpha-7 nicotinic acetylcholine receptor agonist disclosed herein that also binds to a 5-HT$_3$ receptor and dampens, inhibits or otherwise prevents a biological response mediated by the 5-HT$_3$ receptor. Thus, an activator of an alpha-7 nicotinic acetylcholine receptor activity having 5-HT$_3$ receptor inhibitory activity has affinity but no efficacy for its cognate 5-HT$_3$ receptor. Once bound, however, an activator of an alpha-7 nicotinic acetylcholine receptor activity having 5-HT$_3$ receptor inhibitory activity inhibit the function of agonists, inverse agonists, and partial agonists. An activator of an alpha-7 nicotinic acetylcholine receptor activity having 5-HT$_3$ receptor inhibitory activity disclosed herein can mediate its effects by binding to an active orthosteric site or by binding to an allosteric site on a 5-HT$_3$ receptor, or an activator of an alpha-7 nicotinic acetylcholine receptor activity having 5-HT$_3$ receptor inhibitory activity disclosed herein may interact at unique binding sites not normally involved in the biological regulation of 5-HT$_3$ receptor activity. An activator of an alpha-7 nicotinic acetylcholine receptor activity having 5-HT$_3$ receptor inhibitory activity disclosed herein may be reversible or irreversible depending on the longevity of the antagonist-receptor complex, which, in turn, depends on the nature of antagonist-receptor binding.

An activator of an alpha-7 nicotinic acetylcholine receptor activity having 5-HT$_3$ receptor inhibitory activity disclosed herein can have full antagonistic activity at a 5-HT$_3$ receptor, a partial antagonistic activity at a 5-HT$_3$ receptor, or a co-agonist antagonistic activity at a 5-HT$_3$ receptor. An activator of an alpha-7 nicotinic acetylcholine receptor activity having 5-HT$_3$ full receptor antagonistic activity at a 5-HT$_3$ receptor bind to and inhibits the maximum biological response mediated by a given 5-HT$_3$ receptor. An activator of an alpha-7 nicotinic acetylcholine receptor activity having 5-HT$_3$ partial receptor antagonistic activity at a 5-HT$_3$ receptor bind to and dampens, but does not completely inhibit the biological response mediated by a given 5-HT$_3$ receptor, even at maximal receptor occupancy. An activator of an alpha-7 nicotinic acetylcholine receptor activity having 5-HT$_3$ full receptor co-antagonistic activity at a 5-HT$_3$ receptor works together with other 5-HT$_3$ receptor co-antagonists to produce the desired blocking effect of a biological response.

An activator of an alpha-7 nicotinic acetylcholine receptor activity having 5-HT$_3$ receptor antagonistic activity disclosed herein can be an activator of an alpha-7 nicotinic acetylcholine receptor activity having 5-HT$_3$ full receptor pan-antagonistic activity at a 5-HT$_3$ receptor or an activator of an alpha-7 nicotinic acetylcholine receptor activity having 5-HT$_3$ selective receptor pan-antagonistic activity at a 5-HT$_3$ receptor. An activator of an alpha-7 nicotinic acetylcholine receptor activity having 5-HT$_3$ pan-receptor antagonistic activity binds to and dampens, inhibits, or otherwise prevents a biological response mediated by any 5-HT-3 receptor irrespective of subunit composition. An activator of an alpha-7 nicotinic acetylcholine receptor activity having 5-HT$_3$ selective receptor antagonistic activity binds selective to a specific type of 5-HT$_3$ receptor and dampening, inhibiting or otherwise preventing a biological response via these specific 5-HT$_3$ receptors. For example, an activator of an alpha-7 nicotinic acetylcholine receptor activity having 5-HT$_3$ selective receptor antagonistic activity can bind to and dampen, inhibit or otherwise prevent a biological response from only 5-HT$_3$ homopentameric receptors, or only 5-HT$_3$ heteropentameric receptors, or only 5-HT$_3$ heteropentameric receptors of certain subunit composition, such as, e.g., 5-HT$_{3AC}$ heteropentameric receptors, 5-HT$_{3AD}$ heteropentameric receptors, or 5-HT$_{3AE}$ heteropentameric receptors.

An activator of an alpha-7 nicotinic acetylcholine receptor activity having 5-HT$_3$ receptor antagonistic activity disclosed herein includes, without limitation, an activator of an alpha-7 nicotinic acetylcholine receptor activity having antidepressant 5-HT$_3$ receptor antagonistic activity, an activator of an alpha-7 nicotinic acetylcholine receptor activity having antiemetic 5-HT$_3$ receptor antagonistic activity, an activator of an alpha-7 nicotinic acetylcholine receptor activity having antimalarial 5-HT$_3$ receptor antagonistic activity, an activator of an alpha-7 nicotinic acetylcholine receptor activity having antipsychotic 5-HT$_3$ receptor antagonistic activity, and an activator of an alpha-7 nicotinic acetylcholine receptor activity having gastroprokinetic 5-HT$_3$ receptor antagonistic activity The present specification discloses, in part, an activator of an alpha-7 nicotinic acetylcholine receptor activity having 5-HT$_3$ receptor inverse agonistic activity. An activator of an alpha-7 nicotinic acetylcholine receptor activity having 5-HT$_3$ receptor inverse agonistic activity is a compound that binds to a 5-HT$_3$ receptor and reduces, inhibits, or otherwise prevents the constitutive activity of the 5-HT$_3$ receptor. As such, whereas a molecule with 5-HT$_3$ receptor agonistic activity causes a biological response, a molecule with 5-HT$_3$ receptor antagonistic activity blocks the biological response elicited by a 5-HT$_3$ receptor agonist, and a molecule with 5-HT$_3$ receptor inverse agonistic activity exerts the opposite biological response to that of a 5-HT$_3$ receptor agonist, not merely an absence of the biological response as seen with an antagonistic activity. An activator of an alpha-7 nicotinic acetylcholine receptor activity having 5-HT$_3$ receptor inverse agonistic activity includes, without limitation, an activator of an alpha-7 nicotinic acetylcholine receptor activity having 5-HT$_3$ receptor full inverse agonistic activity, an activator of an alpha-7 nicotinic acetylcholine receptor activity having 5-HT$_3$ receptor partial inverse agonistic activity, and an activator of an alpha-7 nicotinic acetylcholine receptor activity having 5-HT$_3$ receptor co-inverse agonistic activity. An activator of an alpha-7 nicotinic acetylcholine receptor activity having 5-HT$_3$ receptor inverse agonistic activity includes, without limitation, an activator of an alpha-7 nicotinic acetylcholine receptor activity having 5-HT$_3$ receptor pan inverse agonistic activity and an activator of an alpha-7 nicotinic acetylcholine receptor activity having 5-HT$_3$ receptor selective inverse agonistic activity.

The present specification discloses, in part, a therapeutically effective amount. With respect to a combination therapy disclosed herein, an activator of alpha-7 nicotinic acetylcholine receptor activity having 5-HT$_3$ receptor inhibitory activity, a 5-HT$_3$ receptor agonist, an activator of an alpha-7 nicotinic acetylcholine receptor activity having 5-HT$_3$ receptor antagonistic activity and an activator of an alpha-7 nicotinic acetylcholine receptor activity having 5-HT$_3$ receptor inverse agonistic activity, collectively called "active agent", are each used or administered in a therapeutically effective amount. A therapeutically effective amount of an active agent present in a combination therapy is an amount sufficient to treat a schizophrenic disorder or pathology. In aspects of this embodiment, a therapeutically effective amount of an active agent present in a combination therapy is an amount sufficient to reduce one or more physiological conditions or symptoms associated with a schizophrenic disorder or pathology or an amount sufficient to protect the individual against one or more physiological conditions or symptoms associated with a schizophrenic disorder or pathology. As used herein, the term "therapeutically effective amount" includes the terms "amount sufficient", "therapeutically sufficient amount", "effective amount", "effective dose", or "therapeutically effective dose" and refers to the minimum amount of an active agent disclosed herein present in a combination therapy disclosed herein necessary to achieve the desired therapeutic effect and includes an amount sufficient to reduce or inhibit one or more physiological conditions or symptoms associated with a schizophrenic disorder or pathology.

In aspects of this embodiment, a therapeutically effective amount of an active agent disclosed herein present in a combination therapy disclosed herein reduces or inhibits one or more physiological conditions or symptoms associated with a schizophrenic disorder or pathology by, e.g., at least 10%, at least 20%, at least 30%, at least 40%, at least 50%, at least 60%, at least 70%, at least 80%, at least 90% or at least 100%. In other aspects of this embodiment, an effective amount of an active agent disclosed herein present in a combination therapy disclosed herein reduces or inhibits one or more physiological conditions or symptoms associated with a schizophrenic disorder or pathology by, e.g., at most 10%, at most 20%, at most 30%, at most 40%, at most 50%, at most 60%, at most 70%, at most 80%, at most 90% or at most 100%. In yet other aspects of this embodiment, an effective amount of an active agent disclosed herein present in a combination therapy disclosed herein reduces or inhibits one or more physiological conditions or symptoms associated with a schizophrenic disorder or pathology by, e.g., about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 20%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%. In still other aspects of this embodiment, an effective amount of an active agent disclosed herein present in a combination therapy disclosed herein reduces or inhibits one or more physiological conditions or symptoms associated with a schizophrenic disorder or pathology for, e.g., at least one week, at least one month, at least two months, at least three months, at least four months, at least five months, at least six months, at least seven months, at least eight months, at least nine months, at least ten months, at least eleven months, or at least twelve months.

In some embodiments, a therapeutic effective amount a therapeutic effective amount of a combined therapy comprising about 0.1 mg to about 1,000 mg of an alpha-7 nicotinic acetylcholine receptor activity having 5-HT$_3$ receptor inhibitory activity and about 0.1 mg to about 1,000 mg of a 5-HT$_3$ receptor agonist. In aspects of these embodiments, a therapeutic effective amount a therapeutic effective amount of a combined therapy comprising about 0.25 mg to about 750 mg, about 0.5 mg to about 500 mg, about 0.75 mg to about 250 mg, or about 1 mg to about 250 mg, of an alpha-7 nicotinic acetylcholine receptor activity having 5-HT$_3$ receptor inhibitory activity and about 0.25 mg to about 750 mg, about 0.5 mg to about 500 mg, about 0.75 mg to about 250 mg, or about 1 mg to about 250 mg, of a 5-HT$_3$ receptor agonist.

In some embodiments, a therapeutic effective amount of a combined therapy comprising about 0.1 mg to about 1,000 mg of an activator of an alpha-7 nicotinic acetylcholine receptor activity having 5-HT$_3$ receptor antagonistic activity and about 0.1 mg to about 1,000 mg of a 5-HT$_3$ receptor agonist. In aspects of these embodiments, a therapeutic effective amount of a combined therapy comprising about 0.25 mg to about 750 mg, about 0.5 mg to about 500 mg, about 0.75 mg to about 250 mg, or about 1 mg to about 250 mg, of an activator of an alpha-7 nicotinic acetylcholine receptor activity having 5-HT$_3$ receptor antagonistic activity and about 0.25 mg to about 750 mg, about 0.5 mg to about 500 mg, about 0.75 mg to about 250 mg, or about 1 mg to about 250 mg, of a 5-HT$_3$ receptor agonist.

In some embodiments, a therapeutic effective amount of a combined therapy comprising about 0.1 mg to about 1,000 mg of an activator of an alpha-7 nicotinic acetylcholine receptor activity having 5-HT$_3$ receptor inverse agonistic activity and about 0.1 mg to about 1,000 mg of a 5-HT$_3$ receptor agonist. In aspects of these embodiments, a therapeutic effective amount of a combined therapy comprising about 0.25 mg to about 750 mg, about 0.5 mg to about 500 mg, about 0.75 mg to about 250 mg, or about 1 mg to about 250 mg, of an activator of an alpha-7 nicotinic acetylcholine receptor activity having 5-HT$_3$ receptor inverse agonistic activity and about 0.25 mg to about 750 mg, about 0.5 mg to about 500 mg, about 0.75 mg to about 250 mg, or about 1 mg to about 250 mg, of a 5-HT$_3$ receptor agonist.

In some embodiments, a therapeutic effective amount of a combined therapy comprising about 1 mg to about 100 mg of a Tropisetron and about 0.1 mg to about 5 mg of a Varenicline. In some embodiments, a therapeutic effective amount of a combined therapy comprising about 2 mg to about 75 mg of a Tropisetron and about 0.25 mg to about 4 mg of a Varenicline. In some embodiments, a therapeutic effective amount of a combined therapy comprising about 5 mg to about 50 mg of a Tropisetron and about 0.5 mg to about 2 mg of a Varenicline.

In some embodiments, a therapeutic effective amount of a combined therapy can be one where one, some or all of the active agents are in an optimal therapeutic amount. An optimal therapeutic amount is a quantity of an active agent that will most effectively produce the desired therapeutic effect while remaining in the range of acceptable toxicity.

In some embodiments, a therapeutic effective amount of a combined therapy can be one where one, some or all of the active agents are in a suboptimal therapeutic amount. A suboptimal therapeutic amount a quantity of an active agent that is below the optimal therapeutic amount for that active agent but still provides some degree of a therapeutic effect desired. In aspects of these embodiments, a suboptimal therapeutic amount of an active agent is, e.g., less than 80%, less than 75%, less than 70%, less than 60%, less than 55%, less than 50%, of the optimal therapeutic amount for that active agent. In aspects of these embodiments, a suboptimal therapeutic amount of an active agent is, e.g., about 10% to about 80%, about 20% to about 80%, about 30% to about 80%, about 40% to about 80%, or about 50% to about 80%, of the optimal therapeutic amount for that active agent.

In some embodiments, a therapeutic effective amount of a combined therapy can be one where one, some or all of the active agents are in a non-therapeutic amount. A non-therapeutic amount a quantity of an active agent that is a suboptimal therapeutic amount for that active agent but provides therapeutic effect. In aspects of these embodiments, a non-therapeutic amount of an active agent is, e.g., less than 80%, less than 75%, less than 70%, less than 60%, less than 55%, less than 50%, of the suboptimal therapeutic amount for that active agent. In aspects of these embodiments, a non-therapeutic amount of an active agent is, e.g., about 10% to about 80%, about 20% to about 80%, about 30% to about 80%, about 40% to about 80%, or about 50% to about 80%, of the suboptimal therapeutic amount for that active agent.

In some embodiments, a therapeutic effective amount of a combined therapy comprising an alpha-7 nicotinic acetylcholine receptor activity having 5-HT$_3$ receptor inhibitory activity and a 5-HT$_3$ receptor agonist is one where 1) the amount of an activator of an alpha-7 nicotinic acetylcholine receptor activity having 5-HT$_3$ receptor inhibitory activity is a suboptimal therapeutic amount when administered alone, 2) the amount of a 5-HT$_3$ receptor agonist is a suboptimal therapeutic amount when administered alone, or 3) the amount of an activator of an alpha-7 nicotinic acetylcholine receptor activity having 5-HT$_3$ receptor inhibitory activity and the amount of a 5-HT$_3$ receptor agonist are both suboptimal therapeutic amount when each is administered alone. In aspects of these embodiments, a therapeutic effective amount of a combined therapy comprising an alpha-7 nicotinic acetylcholine receptor activity having 5-HT$_3$ receptor inhibitory activity and a 5-HT$_3$ receptor agonist is one where 1) the amount of an activator of an alpha-7 nicotinic acetylcholine receptor activity having 5-HT$_3$ receptor inhibitory activity is a non-therapeutic amount when administered alone, 2) the amount of a 5-HT$_3$ receptor agonist is a non-therapeutic amount when administered alone, or 3) the amount of an activator of an alpha-7 nicotinic acetylcholine receptor activity having 5-HT$_3$ receptor inhibitory activity and the amount of a 5-HT$_3$ receptor agonist are both non-therapeutic amount when each is administered alone.

In some embodiments, a therapeutic effective amount of a combined therapy comprising an activator of an alpha-7 nicotinic acetylcholine receptor activity having 5-HT$_3$ receptor antagonistic activity and a 5-HT$_3$ receptor agonist is one where 1) the amount of an activator of an alpha-7 nicotinic acetylcholine receptor activity having 5-HT$_3$ receptor antagonistic activity is a suboptimal therapeutic amount when administered alone, 2) the amount of a 5-HT$_3$ receptor agonist is a suboptimal therapeutic amount when administered alone, or 3) the amount of an activator of an alpha-7 nicotinic acetylcholine receptor activity having 5-HT$_3$ receptor antagonistic activity and the amount of a 5-HT$_3$ receptor agonist are both suboptimal therapeutic amount when each is administered alone. In aspects of these embodiments, a therapeutic effective amount of a combined therapy comprising an activator of an alpha-7 nicotinic acetylcholine receptor activity having 5-HT$_3$ receptor antagonistic activity and a 5-HT$_3$ receptor agonist is one where 1) the amount of an activator of an alpha-7 nicotinic acetylcholine receptor activity having 5-HT$_3$ receptor antagonistic activity is a non-therapeutic amount when administered alone, 2) the amount of a 5-HT$_3$ receptor agonist is a non-therapeutic amount when administered alone, or 3) the amount of an activator of an alpha-7 nicotinic acetylcholine receptor activity having 5-HT$_3$ receptor antagonistic activity and the amount of a 5-HT$_3$ receptor agonist are both non-therapeutic amounts when each is administered alone.

In some embodiments, a therapeutic effective amount of a combined therapy comprising an alpha-7 nicotinic acetylcholine receptor agonist having 5-HT$_3$ receptor antagonistic activity and a 5-HT$_3$ receptor agonist is one where 1) the amount of an alpha-7 nicotinic acetylcholine receptor agonist having 5-HT$_3$ receptor antagonistic activity is a suboptimal therapeutic amount when administered alone, 2) the amount of a 5-HT$_3$ receptor agonist is a suboptimal therapeutic amount when administered alone, or 3) the amount of an alpha-7 nicotinic acetylcholine receptor agonist having 5-HT$_3$ receptor antagonistic activity and the amount of a 5-HT$_3$ receptor agonist are both suboptimal therapeutic amount when each is administered alone. In aspects of these embodiments, a therapeutic effective amount of a combined therapy comprising an alpha-7 nicotinic acetylcholine receptor agonist having 5-HT$_3$ receptor antagonistic activity and a 5-HT$_3$ receptor agonist is one where 1) the amount of an alpha-7 nicotinic acetylcholine receptor agonist having 5-HT$_3$ receptor antagonistic activity is a non-therapeutic amount when administered alone, 2) the amount of a 5-HT$_3$ receptor agonist is a non-therapeutic amount when administered alone, or 3) the amount of an alpha-7 nicotinic acetylcholine receptor agonist having 5-HT$_3$ receptor antagonistic activity and the amount of a 5-HT$_3$ receptor agonist are both non-therapeutic amounts when each is administered alone.

In some embodiments, a therapeutic effective amount of a combined therapy comprising an activator of an alpha-7 nicotinic acetylcholine receptor activity having 5-HT$_3$ receptor inverse agonistic activity and a 5-HT$_3$ receptor agonist is one where 1) the amount of an activator of an alpha-7 nicotinic acetylcholine receptor activity having 5-HT$_3$ receptor inverse agonistic activity is a suboptimal therapeutic amount when administered alone, 2) the amount of a 5-HT$_3$ receptor agonist is a suboptimal therapeutic amount when administered alone, or 3) the amount of an activator of an alpha-7 nicotinic acetylcholine receptor activity having 5-HT$_3$ receptor inverse agonistic activity and the amount of a 5-HT$_3$ receptor agonist are both suboptimal therapeutic amount when each is administered alone. In aspects of these embodiments, a therapeutic effective amount of a combined therapy comprising an activator of an alpha-7 nicotinic acetylcholine receptor activity having 5-HT$_3$ receptor inverse agonistic activity and a 5-HT$_3$ receptor agonist is one where 1) the amount of an activator of an alpha-7 nicotinic acetylcholine receptor activity having 5-HT$_3$ receptor inverse agonistic activity is a non-therapeutic amount when administered alone, 2) the amount of a 5-HT$_3$ receptor agonist is a non-therapeutic amount when administered alone, or 3) the amount of an activator of an alpha-7 nicotinic acetylcholine receptor activity having 5-HT$_3$ receptor inverse agonistic activity and the amount of a 5-HT$_3$ receptor agonist are both non-therapeutic amounts when each is administered alone.

In some embodiments, a therapeutic effective amount of a combined therapy comprising an alpha-7 nicotinic acetylcholine receptor agonist having 5-HT$_3$ receptor inverse agonistic activity and a 5-HT$_3$ receptor agonist is one where 1) the amount of an alpha-7 nicotinic acetylcholine receptor agonist having 5-HT$_3$ receptor inverse agonistic activity is a suboptimal therapeutic amount when administered alone, 2) the amount of a 5-HT$_3$ receptor agonist is a suboptimal therapeutic amount when administered alone, or 3) the amount of an alpha-7 nicotinic acetylcholine receptor agonist having 5-HT$_3$ receptor inverse agonistic activity and the amount of a 5-HT$_3$ receptor agonist are both suboptimal therapeutic amount when each is administered alone. In aspects of these embodiments, a therapeutic effective amount of a combined therapy comprising an alpha-7 nicotinic acetylcholine receptor agonist having 5-HT$_3$ receptor inverse agonistic activity and a 5-HT$_3$ receptor agonist is one where 1) the amount of an alpha-7 nicotinic acetylcholine receptor agonist having 5-HT$_3$ receptor inverse agonistic activity is a non-therapeutic amount when administered alone, 2) the amount of a 5-HT$_3$ receptor agonist is a non-therapeutic amount when administered alone, or 3) the amount of an alpha-7 nicotinic acetylcholine receptor agonist having 5-HT$_3$ receptor inverse agonistic activity and the amount of a 5-HT$_3$ receptor agonist are both non-therapeutic amounts when each is administered alone.

In some embodiments, a therapeutic effective amount of a combined therapy comprising a Tropisetron and a Varenicline is one where 1) the amount of a Tropisetron is a suboptimal therapeutic amount when administered alone, 2) the amount of a Varenicline is a suboptimal therapeutic amount when administered alone, or 3) the amount of a Tropisetron and the amount of a Varenicline are both suboptimal therapeutic amounts when each is administered alone. In aspects of these embodiments, a therapeutic effective amount of a combined therapy comprising a Tropisetron and a Varenicline is one where 1) the amount of a Tropisetron is a non-therapeutic amount when administered alone, 2) the amount of a Varenicline is a non-therapeutic amount when administered alone, or 3) the amount of a Tropisetron and the amount of a Varenicline are both non-therapeutic amounts when each is administered alone.

The actual therapeutic effective amount of an active agent disclosed herein present in a combination therapy disclosed herein to be used or administered to an individual can be determined by a person of ordinary skill in the art by taking into account factors, including, without limitation, the type of schizophrenic disorder or pathology, the particular physiological conditions or symptoms associated with the schizophrenic disorder or pathology, the cause of the schizophrenic disorder or pathology, the severity of the schizophrenic disorder or pathology, the degree of relief desired for schizophrenic disorder or pathology, the duration of relief desired for schizophrenic disorder or pathology, the particular active agent used in a combination therapy, the rate of excretion of the particular active agent used in a combination therapy, the pharmacodynamics of the particular active agent used present in a combination therapy, the nature of the other compounds to be included in the combination therapy, the particular route of administration used, the particular characteristics, history and risk factors of the individual, such as, e.g., age, weight, general health and the like, or any combination thereof. Additionally, where repeated administration of a combination therapy disclosed herein is used, the actual therapeutically effective amount will further depend upon factors, including, without limitation, the frequency of administration, the half-life of an active agent disclosed herein present in a combination therapy, or any combination thereof. It is known by a person of ordinary skill in the art that an effective amount of an active agent disclosed herein present in a combination therapy can be extrapolated from in vitro assays and in vivo administration studies using animal models prior to administration to humans. Wide variations in the necessary effective amount are to be expected in view of the differing efficiencies of the various routes of administration. For instance, oral use or administration generally would be expected to require higher dosage levels than use or administration by intravenous or intravitreal injection. Variations in these dosage levels can be adjusted using standard empirical routines of optimization, which are well-known to a person of ordinary skill in the art. The precise therapeutically effective dosage levels and patterns are preferably determined by the attending healthcare professional in consideration of the above-identified factors.

Dosing can be single dosage or cumulative (serial dosing), and can be readily determined by one skilled in the art. For instance, treatment of a schizophrenic disorder or pathology may comprise a one-time administration of a combination therapy disclosed herein. As a non-limiting example, a combination therapy can be administered once to an individual, e.g., as a single injection or deposition.

Alternatively, treatment of a schizophrenic disorder or pathology may comprise multiple administrations of a combination therapy disclosed herein carried out over a range of time periods, such as, e.g., daily, once every few days, weekly, monthly, or yearly. As a non-limiting example, a combination therapy can be administered one, two, three, four, five or six times yearly to an individual. The timing of administration can vary from individual to individual, depending upon such factors as the severity of an individual's symptoms. For example, a combination therapy can be administered to an individual once every three months for an indefinite period of time, or until the individual no longer requires therapy. A person of ordinary skill in the art will recognize that the condition of the individual can be monitored throughout the course of treatment and that use or administration of a combination therapy disclosed herein can be adjusted accordingly.

The present specification discloses, in part, a schizophrenic disorder. A schizophrenic disorder is a group of psychiatric disorders characterized by the deterioration in the functional interaction between thought, emotion, and behavior leading to a wide array of disturbances in cognition, perception, and mood. Characteristically, an individual with a schizophrenic disorder exhibits a gross distortion of reality, significant disturbances of language and cognitive function, extensive withdrawal from social interaction, disorganization, and fragmentation of thought, altered perception, and inappropriate emotional reaction.

The clinical features of a schizophrenic disorder can be clustered into three symptom groups, positive symptoms, negative symptom, and cognitive symptoms. Positive symptoms are classified as fixed, false feelings or behaviors involving real-life situations that could be true but are simply manifestations of psychosis, such as, e.g., delusions, hallucinations, paranoia, thought disorders (disorganized thinking, speech or behavior, neologism) and movement disorders (clumsy, uncoordinated, repetitious movements, catatonia). Negative symptoms are classified as deficits or reductions in normal emotion and behavior, such as, e.g., affective disturbances (immobile expression, monotonous voice), reduced interest or lack of pleasure in everyday activities (anhedonia, like depression), lack of motivation (avolition), decreased ability to initiate and sustain planned activity, poverty of speech (alogia), infrequent speech (even when forced to interact), and social withdrawal. Cognitive symptoms are classified as deficits in the mental processes of comprehension, judgement, memory, and reasoning, such as, e.g., problems in selective attention, working memory, executive function, episodic memory, language comprehension and social-emotional processing.

Non-limiting examples of a schizophrenic disorder include schizophrenia, a schizophreniform disorder, schizoaffective disorder, and a schizotypal personality disorder. A schizophrenia is one where an individual has symptoms of schizophrenia that last for six months or more. A schizoaffective disorder is one where an individual has symptoms of both schizophrenia and a mood disorder, such as depression or bipolar disorder. A schizophreniform disorder is one where an individual has symptoms of schizophrenia, but the symptoms last for less than six months. A schizotypal personality disorder is a schizophrenia-like condition characterized by defects in interpersonal relationships and disturbed thought patterns, appearance, behavior that are not severe enough to meet the clinical criteria of schizophrenia.

A schizophrenia can be divided into five subtypes based on the type and frequency of positive and negative symptoms, namely disorganized, catatonic, paranoid, undifferentiated and residual. Disorganized (hebephrenic) schizophrenia is characterized by individuals having disorganized, incoherent thinking; shallow, flat, inappropriate, and/or silly emotional responses to a situation (affect); and regressive behavior without systematized delusions. Catatonic schizophrenia is characterized by individuals having psychomotor disturbance which may involve stupor, rigidity, excitement, negativism, or bizarre posturing, or an alteration among these behaviors; associated features include mutism, stereotypy, and waxy flexibility. Paranoid schizophrenia is characterized by individuals having persecutory or grandiose delusions, delusional jealousy, or hallucinations with persecutory or grandiose content. Undifferentiated schizophrenia is characterized by individuals having positive and negative symptoms of schizophrenia but which do not meet the specific criteria for the paranoid, disorganized, or catatonic subtypes. Residual schizophrenia is characterized by individuals having a previous schizophrenic episode but do not currently present with any positive symptoms, although negative symptoms may persist.

In addition to these five symptomatic subtypes, individuals can also be classified based on other criteria including susceptibility, initial event, duration, antipsychotic drug resistance and cognitive symptoms. For example, an individual who begins experiencing some psychotic symptoms, but these symptoms can also occur in people who will never develop a schizophrenic disorder is classified as being at ultra-high risk (UHR) or at-risk mental state (ARMS) for psychosis. An individual who experiences psychotic symptoms or an episode of schizophrenic disorder for the first time is classified as having first-episode psychosis (FEP). An individual suffering from a schizophrenic disorder whose positive and negative symptoms are being successfully being managed with a therapy comprising an antipsychotic medication is classified as having a chronic treatment responsive schizophrenia. An individual suffering from a schizophrenic disorder who after an initial period of therapeutic success becomes resistant to an antipsychotic medication is classified as having a treatment-resistant schizophrenia (TRS). An individual suffering from a schizophrenic disorder whose positive and negative symptoms are being successfully being managed with a therapy comprising an antipsychotic medication but is still afflicted with cognitive symptoms is classified as having a cognitive impairment associated with schizophrenia (CIAS).

In one embodiment, a method of treating a schizophrenic disorder comprises, consists essentially of, or consists of administering a combined therapy comprising, consisting essentially of, or consisting of one or more activators of an alpha-7 nicotinic acetylcholine receptor activity having 5-HT$_3$ receptor inhibitory activity and one or more activators of 5-HT$_3$ receptor activity. In aspects of this embodiment, a method of treating a schizophrenia comprises, consists essentially of, or consists of administering a combined therapy comprising, consisting essentially of, or consisting of one or more activators of an alpha-7 nicotinic acetylcholine receptor activity having 5-HT$_3$ receptor inhibitory activity and one or more activators of 5-HT$_3$ receptor activity. In other aspects of this embodiment, a method of treating a treatment-resistant schizophrenia comprises, consists essentially of, or consists of administering a combined therapy comprising, consisting essentially of, or consisting of one or more activators of an alpha-7 nicotinic acetylcholine receptor activity having 5-HT$_3$ receptor inhibitory activity and one or more activators of 5-HT$_3$ receptor activity. In yet other aspects of this embodiment, a method of treating a cognitive impaired schizophrenia comprises, consists essentially of, or consists of administering a combined therapy comprising, consisting essentially of, or consisting of one or more activators of an alpha-7 nicotinic acetylcholine receptor activity having 5-HT$_3$ receptor inhibitory activity and one or more activators of 5-HT$_3$ receptor activity.

In one embodiment, a method of treating a schizophrenic disorder comprises, consists essentially of, or consists of administering a combined therapy comprising, consisting essentially of, or consisting of a therapeutically effective amount of one or more activators of an alpha-7 nicotinic acetylcholine receptor activity having 5-HT$_3$ receptor inhibitory activity and a therapeutically effective amount of one or more activators of 5-HT$_3$ receptor activity. In aspects of this embodiment, a method of treating a schizophrenia comprises, consists essentially of, or consists of administering a combined therapy comprising, consisting essentially of, or consisting of a therapeutically effective amount of one or more activators of an alpha-7 nicotinic acetylcholine receptor activity having 5-HT$_3$ receptor inhibitory activity and a therapeutically effective amount of one or more activators of 5-HT$_3$ receptor activity. In other aspects of this embodiment, a method of treating a treatment-resistant schizophrenia comprises, consists essentially of, or consists of administering a combined therapy comprising, consisting essentially of, or consisting of a therapeutically effective amount of one or more activators of an alpha-7 nicotinic acetylcholine receptor activity having 5-HT$_3$ receptor inhibitory activity and a therapeutically effective amount of one or more activators of 5-HT$_3$ receptor activity. In yet other aspects of this embodiment, a method of treating a cognitive impaired schizophrenia comprises, consists essentially of, or consists of administering a combined therapy comprising, consisting essentially of, or consisting of a therapeutically effective amount of one or more activators of an alpha-7 nicotinic acetylcholine receptor activity having 5-HT$_3$ receptor inhibitory activity and a therapeutically effective amount of one or more activators of 5-HT$_3$ receptor activity. In some embodiments, a therapeutic effective amount of one or more activators of an alpha-7 nicotinic acetylcholine receptor activity having 5-HT$_3$ receptor inhibitory activity is an amount that is a suboptimal therapeutic amount when administer alone. In some embodiments, a therapeutic effective amount of one or more activators of an alpha-7 nicotinic acetylcholine receptor activity having 5-HT$_3$ receptor inhibitory activity is an amount that is a non-therapeutic amount when administer alone. In some embodiments, a therapeutic effective amount of one or more 5-HT$_3$ receptor agonists is an amount that is a suboptimal therapeutic amount. In some embodiments, a therapeutic effective amount of one or more 5-HT$_3$ receptor agonists is an amount that is a non-therapeutic amount when administer alone. In some embodiments, a therapeutic effective amount of one or more activators of an alpha-7 nicotinic acetylcholine receptor activity having 5-HT$_3$ receptor inhibitory activity is an amount that is a suboptimal therapeutic amount when administer alone and a therapeutic effective amount of one or more 5-HT$_3$ receptor agonists is an amount that is a suboptimal therapeutic amount when administer alone. In some embodiments, a therapeutic effective amount of one or more activators of an alpha-7 nicotinic acetylcholine receptor activity having 5-HT$_3$ receptor inhibitory activity is an amount that is a non-therapeutic amount when administer alone and a therapeutic effective amount of one or more 5-HT$_3$ receptor agonists is an amount that is a non-therapeutic amount when administer alone.

In one embodiment, a method of treating a schizophrenic disorder comprises, consists essentially of, or consists of administering a combined therapy comprising, consisting essentially of, or consisting of one or more alpha-7 nicotinic acetylcholine receptor agonists having 5-HT$_3$ receptor antagonistic activity and one or more 5-HT$_3$ receptor agonists. In aspects of this embodiment, a method of treating a schizophrenia comprises, consists essentially of, or consists of administering a combined therapy comprising, consisting essentially of, or consisting of one or more alpha-7 nicotinic acetylcholine receptor agonists having 5-HT$_3$ receptor antagonistic activity and one or more 5-HT$_3$ receptor agonists. In other aspects of this embodiment, a method of treating a treatment-resistant schizophrenia comprises, consists essentially of, or consists of administering a combined therapy comprising, consisting essentially of, or consisting of one or more alpha-7 nicotinic acetylcholine receptor agonists having 5-HT$_3$ receptor antagonistic activity and one or more 5-HT$_3$ receptor agonists. In yet other aspects of this embodiment, a method of treating a cognitive impaired schizophrenia comprises, consists essentially of, or consists of administering a combined therapy comprising, consisting essentially of, or consisting of one or more alpha-7 nicotinic acetylcholine receptor agonists having 5-HT$_3$ receptor antagonistic activity and one or more 5-HT$_3$ receptor agonists.

In one embodiment, a method of treating a schizophrenic disorder comprises, consists essentially of, or consists of administering a combined therapy comprising, consisting essentially of, or consisting of a therapeutically effective amount of one or more alpha-7 nicotinic acetylcholine receptor agonists having 5-HT$_3$ receptor antagonistic activity and a therapeutically effective amount of one or more 5-HT$_3$ receptor agonists. In aspects of this embodiment, a method of treating a schizophrenia comprises, consists essentially of, or consists of administering a combined therapy comprising, consisting essentially of, or consisting of a therapeutically effective amount of one or more alpha-7 nicotinic acetylcholine receptor agonists having 5-HT$_3$ receptor antagonistic activity and a therapeutically effective amount of one or more 5-HT$_3$ receptor agonists. In other aspects of this embodiment, a method of treating a treatment-resistant schizophrenia comprises, consists essentially of, or consists of administering a combined therapy comprising, consisting essentially of, or consisting of a therapeutically effective amount of one or more alpha-7 nicotinic acetylcholine receptor agonists having 5-HT$_3$ receptor antagonistic activity and a therapeutically effective amount of one or more 5-HT$_3$ receptor agonists. In yet other aspects of this embodiment, a method of treating a cognitive impaired schizophrenia comprises, consists essentially of, or consists of administering a combined therapy comprising, consisting essentially of, or consisting of a therapeutically effective amount of one or more alpha-7 nicotinic acetylcholine receptor agonists having 5-HT$_3$ receptor antagonistic activity and a therapeutically effective amount of one or more 5-HT$_3$ receptor agonists. In some embodiments, a therapeutic effective amount of one or more alpha-7 nicotinic acetylcholine receptor agonists having 5-HT$_3$ receptor antagonistic activity is an amount that is a suboptimal therapeutic amount when administer alone. In some embodiments, a therapeutic effective amount of one or more alpha-7 nicotinic acetylcholine receptor agonists having 5-HT$_3$ receptor antagonistic activity is an amount that is a non-therapeutic amount when administer alone. In some embodiments, a therapeutic effective amount of one or more 5-HT$_3$ receptor agonists is an amount that is a suboptimal therapeutic amount when administer alone. In some embodiments, a therapeutic effective amount of one or more 5-HT$_3$ receptor agonists is an amount that is a non-therapeutic amount when administer alone. In some embodiments, a therapeutic effective amount of one or more alpha-7 nicotinic acetylcholine receptor agonists having 5-HT$_3$ receptor antagonistic activity is an amount that is a suboptimal therapeutic amount when administer alone and a therapeutic effective amount of one or more 5-HT$_3$ receptor agonists is an amount that is a suboptimal therapeutic amount when administer alone. In some embodiments, a therapeutic effective amount of one or more alpha-7 nicotinic acetylcholine receptor agonists having 5-HT$_3$ receptor antagonistic activity is an amount that is a non-therapeutic amount when administer alone and a therapeutic effective amount of one or more 5-HT$_3$ receptor agonists is an amount that is a non-therapeutic amount when administer alone.

In one embodiment, a method of treating a schizophrenic disorder comprises, consists essentially of, or consists of administering a combined therapy comprising, consisting essentially of, or consisting of one or more alpha-7 nicotinic acetylcholine receptor agonists having 5-HT$_3$ receptor inverse agonistic activity and one or more 5-HT$_3$ receptor agonists. In aspects of this embodiment, a method of treating a schizophrenia comprises, consists essentially of, or consists of administering a combined therapy comprising, consisting essentially of, or consisting of one or more alpha-7 nicotinic acetylcholine receptor agonists having 5-HT$_3$ receptor inverse agonistic activity and one or more 5-HT$_3$ receptor agonists. In other aspects of this embodiment, a method of treating a treatment-resistant schizophrenia comprises, consists essentially of, or consists of administering a combined therapy comprising, consisting essentially of, or consisting of one or more alpha-7 nicotinic acetylcholine receptor agonists having 5-HT$_3$ receptor inverse agonistic activity and one or more 5-HT$_3$ receptor agonists. In yet other aspects of this embodiment, a method of treating a cognitive impaired schizophrenia comprises, consists essentially of, or consists of administering a combined therapy comprising, consisting essentially of, or consisting alpha-7 nicotinic acetylcholine receptor agonists having 5-HT$_3$ receptor inverse agonistic activity and one or more 5-HT$_3$ receptor agonists.

In one embodiment, a method of treating a schizophrenic disorder comprises, consists essentially of, or consists of administering a combined therapy comprising, consisting essentially of, or consisting of a therapeutically effective amount of one or more alpha-7 nicotinic acetylcholine receptor agonists having 5-HT$_3$ receptor inverse agonistic activity and a therapeutically effective amount of one or more 5-HT$_3$ receptor agonists. In aspects of this embodiment, a method of treating a schizophrenia comprises, consists essentially of, or consists of administering a combined therapy comprising, consisting essentially of, or consisting of a therapeutically effective amount alpha-7 nicotinic acetylcholine receptor agonists having 5-HT$_3$ receptor inverse agonistic activity and a therapeutically effective amount of one or more 5-HT$_3$ receptor agonists. In other aspects of this embodiment, a method of treating a treatment resistant schizophrenia comprises, consists essentially of, or consists of administering a combined therapy comprising, consisting essentially of, or consisting of a therapeutically effective amount alpha-7 nicotinic acetylcholine receptor agonists having 5-HT$_3$ receptor inverse agonistic activity and a therapeutically effective amount of one or more 5-HT$_3$ receptor agonists. In yet other aspects of this embodiment, a method of treating a cognitive impaired schizophrenia comprises, consists essentially of, or consists of administering a combined therapy comprising, consisting essentially of, or consisting of a therapeutically effective amount of one or more alpha-7 nicotinic acetylcholine receptor agonists having 5-HT$_3$ receptor inverse agonistic activity and a therapeutically effective amount of one or more 5-HT$_3$ receptor agonists. In some embodiments, a therapeutic effective amount of one or more alpha-7 nicotinic acetylcholine receptor agonists having 5-HT$_3$ receptor inverse agonistic activity is an amount that is a suboptimal therapeutic amount when administer alone. In some embodiments, a therapeutic effective amount of one or more alpha-7 nicotinic acetylcholine receptor agonists having 5-HT$_3$ receptor inverse agonistic activity is an amount that is a non-therapeutic amount when administer alone. In some embodiments, a therapeutic effective amount of one or more 5-HT$_3$ receptor agonists is an amount that is a suboptimal therapeutic amount when administer alone. In some embodiments, a therapeutic effective amount of one or more 5-HT$_3$ receptor agonists is an amount that is a non-therapeutic amount when administer alone. In some embodiments, a therapeutic effective amount of one or more alpha-7 nicotinic acetylcholine receptor agonists having 5-HT$_3$ receptor inverse agonistic activity is an amount that is a suboptimal therapeutic amount when administer alone and a therapeutic effective amount of one or more 5-HT$_3$ receptor agonists is an amount that is a suboptimal therapeutic amount when administer alone. In some embodiments, a therapeutic effective amount of one or more alpha-7 nicotinic acetylcholine receptor agonists having 5-HT$_3$ receptor inverse agonistic activity is an amount that is a non-therapeutic amount when administer alone and a therapeutic effective amount of one or more 5-HT$_3$ receptor agonists is an amount that is a non-therapeutic amount when administer alone.

In a preferred embodiment, a method of treating a schizophrenic disorder comprises, consists essentially of, or consists of administering a combined therapy comprising, consisting essentially of, or consisting of Varenicline and Tropisetron. In aspects of this embodiment, a method of treating a schizophrenia comprises, consists essentially of, or consists of administering a combined therapy comprising, consisting essentially of, or consisting of Varenicline and Tropisetron. In other aspects of this embodiment, a method of treating a treatment resistant schizophrenia comprises, consists essentially of, or consists of administering a combined therapy comprising, consisting essentially of, or consisting of Varenicline and Tropisetron. In yet other aspects of this embodiment, a method of treating a cognitive impaired schizophrenia comprises, consists essentially of, or consists of administering a combined therapy comprising, consisting essentially of, or consisting of Varenicline and Tropisetron.

In a more preferred embodiment, a method of treating a schizophrenic disorder comprises, consists essentially of, or consists of administering a combined therapy comprising, consisting essentially of, or consisting of a therapeutically effective amount of Varenicline and a therapeutically effective amount of Tropisetron. In aspects of this embodiment, a method of treating a schizophrenia comprises, consists essentially of, or consists of administering a combined therapy comprising, consisting essentially of, or consisting of a therapeutically effective amount of Varenicline and a therapeutically effective amount of Tropisetron. In other aspects of this embodiment, a method of treating a treatment resistant schizophrenia comprises, consists essentially of, or consists of administering a combined therapy comprising, consisting essentially of, or consisting of a therapeutically effective amount of Varenicline and a therapeutically effective amount of Tropisetron. In yet other aspects of this embodiment, a method of treating a cognitive impaired schizophrenia comprises, consists essentially of, or consists of administering a combined therapy comprising, consisting essentially of, or consisting of a therapeutically effective amount of Varenicline and a therapeutically effective amount of Tropisetron. In some embodiments, a therapeutic effective amount of a Tropisetron is an amount that is a suboptimal therapeutic amount when administer alone. In some embodiments, a therapeutic effective amount of a Tropisetron is an amount that is a non-therapeutic amount when administer alone. In some embodiments, a therapeutic effective amount of a Varenicline is an amount that is a suboptimal therapeutic amount when administer alone. In some embodiments, a therapeutic effective amount of a Varenicline is an amount that is a non-therapeutic amount when administer alone. In some embodiments, a therapeutic effective amount of a Tropisetron is an amount that is a suboptimal therapeutic amount when administer alone and a therapeutic effective amount of a Varenicline is an amount that is a suboptimal therapeutic amount when administer alone. In some embodiments, a therapeutic effective amount of a Tropisetron is an amount that is a non-therapeutic amount when administer alone and a therapeutic effective amount of a Varenicline is an amount that is a non-therapeutic amount when administer alone.

In one embodiment, a combined therapy comprising, consists essentially of, or consists of one or more activators of an alpha-7 nicotinic acetylcholine receptor activity having 5-HT$_3$ receptor inhibitory activity and one or more activators of 5-HT$_3$ receptor activity for use in treating a schizophrenic disorder. In aspects of this embodiment, a combined therapy comprising, consists essentially of, or consists of one or more activators of an alpha-7 nicotinic acetylcholine receptor activity having 5-HT$_3$ receptor inhibitory activity and one or more activators of 5-HT$_3$ receptor activity for use in treating a schizophrenia. In other aspects of this embodiment, a combined therapy comprising, consists essentially of, or consists of one or more activators of an alpha-7 nicotinic acetylcholine receptor activity having 5-HT$_3$ receptor inhibitory activity and one or more activators of 5-HT$_3$ receptor activity for use in treating a treatment resistant schizophrenia. In yet other aspects of this embodiment, a combined therapy comprising, consists essentially of, or consists of one or more activators of an alpha-7 nicotinic acetylcholine receptor activity having 5-HT$_3$ receptor inhibitory activity and one or more activators of 5-HT$_3$ receptor activity for use in treating cognitive impairment associated with schizophrenia.

In one embodiment, a combined therapy comprising, consists essentially of, or consists of a therapeutically effective amount of one or more activators of an alpha-7 nicotinic acetylcholine receptor activity having 5-HT$_3$ receptor inhibitory activity and a therapeutically effective amount of one or more activators of 5-HT$_3$ receptor activity for use in treating a schizophrenic disorder. In aspects of this embodiment, a combined therapy comprising, consists essentially of, or consists of a therapeutically effective amount of one or more activators of an alpha-7 nicotinic acetylcholine receptor activity having 5-HT$_3$ receptor inhibitory activity and a therapeutically effective amount of one or more activators of 5-HT$_3$ receptor activity for use in treating a schizophrenia. In other aspects of this embodiment, a combined therapy comprising, consists essentially of, or consists of a therapeutically effective amount of one or more activators of an alpha-7 nicotinic acetylcholine receptor activity having 5-HT$_3$ receptor inhibitory activity and a therapeutically effective amount of one or more activators of 5-HT$_3$ receptor activity for use in treating a treatment resistant schizophrenia. In yet other aspects of this embodiment, a combined therapy comprising, consists essentially of, or consists of a therapeutically effective amount of one or more activators of an alpha-7 nicotinic acetylcholine receptor activity having 5-HT$_3$ receptor inhibitory activity and a therapeutically effective amount of one or more activators of 5-HT$_3$ receptor activity for use in treating a cognitive impairment associated with schizophrenia. In some embodiments, a therapeutic effective amount of one or more activators of an alpha-7 nicotinic acetylcholine receptor activity having 5-HT$_3$ receptor inhibitory activity is an amount that is a suboptimal therapeutic amount when administer alone. In some embodiments, a therapeutic effective amount of one or more activators of an alpha-7 nicotinic acetylcholine receptor activity having 5-HT$_3$ receptor inhibitory activity is an amount that is a non-therapeutic amount when administer alone. In some embodiments, a therapeutic effective amount of one or more 5-HT$_3$ receptor agonists is an amount that is a suboptimal therapeutic amount when administer alone. In some embodiments, a therapeutic effective amount of one or more 5-HT$_3$ receptor agonists is an amount that is a non-therapeutic amount when administer alone. In some embodiments, a therapeutic effective amount of one or more activators of an alpha-7 nicotinic acetylcholine receptor activity having 5-HT$_3$ receptor inhibitory activity is an amount that is a suboptimal therapeutic amount when administer alone and a therapeutic effective amount of one or more 5-HT$_3$ receptor agonists is an amount that is a suboptimal therapeutic amount when administer alone. In some embodiments, a therapeutic effective amount of one or more activators of an alpha-7 nicotinic acetylcholine receptor activity having 5-HT$_3$ receptor inhibitory activity is an amount that is a non-therapeutic amount when administer alone and a therapeutic effective amount of one or more 5-HT$_3$ receptor agonists is an amount that is a non-therapeutic amount when administer alone.

In one embodiment, a combined therapy comprising, consists essentially of, or consists of one or more alpha-7 nicotinic acetylcholine receptor agonists having 5-HT$_3$ receptor antagonistic activity and one or more 5-HT$_3$ receptor agonists for use in treating a schizophrenic disorder. In aspects of this embodiment, a combined therapy comprising, consists essentially of, or consists of one or more alpha-7 nicotinic acetylcholine receptor agonists having 5-HT$_3$ receptor antagonistic activity and one or more 5-HT$_3$ receptor agonists for use in treating a schizophrenia. In other aspects of this embodiment, a combined therapy comprising, consists essentially of, or consists of one or more alpha-7 nicotinic acetylcholine receptor agonists having 5-HT$_3$ receptor antagonistic activity and one or more 5-HT$_3$ receptor agonists for use in treating a treatment resistant schizophrenia. In yet other aspects of this embodiment, a combined therapy comprising, consists essentially of, or consists of one or more alpha-7 nicotinic acetylcholine receptor agonists having 5-HT$_3$ receptor antagonistic activity and one or more 5-HT$_3$ receptor agonists for use in treating a cognitive impairment associated with schizophrenia.

In one embodiment, a combined therapy comprising, consists essentially of, or consists of a therapeutically effective amount of one or more alpha-7 nicotinic acetylcholine receptor agonists having 5-HT$_3$ receptor antagonistic activity and a therapeutically effective amount of one or more 5-HT$_3$ receptor agonists for use in treating a schizophrenic disorder. In aspects of this embodiment, a combined therapy comprising, consists essentially of, or consists of a therapeutically effective amount of one or more alpha-7 nicotinic acetylcholine receptor agonists having 5-HT$_3$ receptor antagonistic activity and a therapeutically effective amount of one or more 5-HT$_3$ receptor agonists for use in treating a schizophrenia. In other aspects of this embodiment, a combined therapy comprising, consists essentially of, or consists of a therapeutically effective amount of one or more alpha-7 nicotinic acetylcholine receptor agonists having 5-HT$_3$ receptor antagonistic activity and a therapeutically effective amount of one or more 5-HT$_3$ receptor agonists for use in treating a treatment resistant schizophrenia. In yet other aspects of this embodiment, a combined therapy comprising, consists essentially of, or consists of a therapeutically effective amount of one or more alpha-7 nicotinic acetylcholine receptor agonists having 5-HT$_3$ receptor antagonistic activity and a therapeutically effective amount of one or more 5-HT$_3$ receptor agonists for use in treating a cognitive impairment associated with schizophrenia. In some embodiments, a therapeutic effective amount of one or more alpha-7 nicotinic acetylcholine receptor agonists having 5-HT$_3$ receptor antagonistic activity is an amount that is a suboptimal therapeutic amount when administer alone. In some embodiments, a therapeutic effective amount of one or more alpha-7 nicotinic acetylcholine receptor agonists having 5-HT$_3$ receptor antagonistic activity is an amount that is a non-therapeutic amount when administer alone. In some embodiments, a therapeutic effective amount of one or more 5-HT$_3$ receptor agonists is an amount that is a suboptimal therapeutic amount when administer alone. In some embodiments, a therapeutic effective amount of one or more 5-HT$_3$ receptor agonists is an amount that is a non-therapeutic amount when administer alone. In some embodiments, a therapeutic effective amount of one or more alpha-7 nico-tinic acetylcholine receptor agonists having 5-HT$_3$ receptor antagonistic activity is an amount that is a suboptimal therapeutic amount when administer alone and a therapeutic effective amount of one or more 5-HT$_3$ receptor agonists is an amount that is a suboptimal therapeutic amount when administer alone. In some embodiments, a therapeutic effective amount of one or more alpha-7 nicotinic acetylcholine receptor agonists having 5-HT$_3$ receptor antagonistic activity is an amount that is a non-therapeutic amount when administer alone and a therapeutic effective amount of one or more 5-HT$_3$ receptor agonists is an amount that is a non-therapeutic amount when administer alone.

In one embodiment, a combined therapy comprising, consists essentially of, or consists of one or more alpha-7 nicotinic acetylcholine receptor agonists having 5-HT$_3$ receptor inverse agonistic activity and one or more 5-HT$_3$ receptor agonists for use in treating a schizophrenic disorder. In aspects of this embodiment, a combined therapy comprising, consists essentially of, or consists of one or more alpha-7 nicotinic acetylcholine receptor agonists having 5-HT$_3$ receptor inverse agonistic activity and one or more 5-HT$_3$ receptor agonists for use in treating a schizophrenia. In other aspects of this embodiment, a combined therapy comprising, consists essentially of, or consists of one or more alpha-7 nicotinic acetylcholine receptor agonists hav-ing 5-HT$_3$ receptor inverse agonistic activity and one or more 5-HT$_3$ receptor agonists for use in treating a treatment resistant schizophrenia. In yet other aspects of this embodi-ment, a combined therapy comprising, consists essentially of, or consists of one or more alpha-7 nicotinic acetylcholine receptor agonists having 5-HT$_3$ receptor inverse agonistic activity and one or more 5-HT$_3$ receptor agonists for use in treating a cognitive impairment associated with schizophre-nia.

In one embodiment, a combined therapy comprising, consists essentially of, or consists of a therapeutically effec-tive amount of one or more alpha-7 nicotinic acetylcholine receptor agonists having 5-HT$_3$ receptor inverse agonistic activity and a therapeutically effective amount of one or more 5-HT$_3$ receptor agonists for use in treating a schizo-phrenic disorder. In aspects of this embodiment, a combined therapy comprising, consists essentially of, or consists of a therapeutically effective amount of one or more alpha-7 nicotinic acetylcholine receptor agonists having 5-HT$_3$ receptor inverse agonistic activity and a therapeutically effective amount of one or more 5-HT$_3$ receptor agonists for use in treating a schizophrenia. In other aspects of this embodiment, a combined therapy comprising, consists essentially of, or consists of a therapeutically effective amount of one or more alpha-7 nicotinic acetylcholine receptor agonists having 5-HT$_3$ receptor inverse agonistic activity and a therapeutically effective amount of one or more 5-HT$_3$ receptor agonists for use in treating a treatment resistant schizophrenia. In yet other aspects of this embodi-ment, a combined therapy comprising, consists essentially of, or consists of a therapeutically effective amount of one or more alpha-7 nicotinic acetylcholine receptor agonists having 5-HT$_3$ receptor inverse agonistic activity and a thera-peutically effective amount of one or more 5-HT$_3$ receptor agonists for use in treating a cognitive impairment associ-ated with schizophrenia. In some embodiments, a therapeu-tic effective amount of one or more alpha-7 nicotinic ace-tylcholine receptor agonists having 5-HT$_3$ receptor inverse agonistic activity is an amount that is a suboptimal thera-peutic amount when administer alone. In some embodi-ments, a therapeutic effective amount of one or more alpha-7 nicotinic acetylcholine receptor agonists having 5-HT$_3$ receptor inverse agonistic activity is an amount that is a non-therapeutic amount when administer alone. In some embodiments, a therapeutic effective amount of one or more 5-HT$_3$ receptor agonists is an amount that is a suboptimal therapeutic amount when administer alone. In some embodi-ments, a therapeutic effective amount of one or more 5-HT$_3$ receptor agonists is an amount that is a non-therapeutic amount when administer alone. In some embodiments, a therapeutic effective amount of one or more alpha-7 nico-tinic acetylcholine receptor agonists having 5-HT$_3$ receptor inverse agonistic activity is an amount that is a suboptimal therapeutic amount when administer alone and a therapeutic effective amount of one or more 5-HT$_3$ receptor agonists is an amount that is a suboptimal therapeutic amount when administer alone. In some embodiments, a therapeutic effec-tive amount of one or more alpha-7 nicotinic acetylcholine receptor agonists having 5-HT$_3$ receptor inverse agonistic activity is an amount that is a non-therapeutic amount when administer alone and a therapeutic effective amount of one or more 5-HT$_3$ receptor agonists is an amount that is a non-therapeutic amount when administer alone.

In a preferred embodiment, a combined therapy compris-ing, consists essentially of, or consists of Varenicline and Tropisetron for use in treating a schizophrenic disorder. In aspects of this embodiment, a combined therapy comprising, consists essentially of, or consists of Varenicline and Tro-pisetron for use in treating a schizophrenia. In other aspects of this embodiment, a combined therapy comprising, con-sists essentially of, or consists of Varenicline and Tropise-tron for use in treating a treatment resistant schizophrenia. In yet other aspects of this embodiment, a combined therapy comprising, consists essentially of, or consists of Varenicline and Tropisetron for use in treating a cognitive impairment associated with schizophrenia.

In a more preferred embodiment, a combined therapy comprising, consists essentially of, or consists of a thera-peutically effective amount of Varenicline and a therapeutically effective amount of Tropisetron for use in treating a schizophrenic disorder. In aspects of this embodiment, a combined therapy comprising, consists essentially of, or consists of a therapeutically effective amount of Varenicline and a therapeutically effective amount of Tropisetron for use in treating a schizophrenia. In other aspects of this embodiment, a combined therapy comprising, consists essentially of, or consists of a therapeutically effective amount of Varenicline and a therapeutically effective amount of Tropisetron for use in treating a treatment resistant schizophrenia. In yet other aspects of this embodiment, a combined therapy comprising, consists essentially of, or consists of a therapeutically effective amount of Varenicline and a therapeutically effective amount of Tropisetron for use in treating a cognitive impairment associated with schizophrenia. In some embodiments, a therapeutic effective amount of a Tropisetron is an amount that is a suboptimal therapeutic amount when administer alone. In some embodiments, a therapeutic effective amount of a Tropisetron is an amount that is a non-therapeutic amount when administer alone. In some embodiments, a therapeutic effective amount of a Varenicline is an amount that is a suboptimal therapeutic amount when administer alone. In some embodiments, a therapeutic effective amount of a Varenicline is an amount that is a non-therapeutic amount when administer alone. In some embodiments, a therapeutic effective amount of a Tropisetron is an amount that is a suboptimal therapeutic amount when administer alone and a therapeutic effective amount of a Varenicline is an amount that is a suboptimal therapeutic amount when administer alone. In some embodiments, a therapeutic effective amount of a Tropisetron is an amount that is a non-therapeutic amount when administer alone and a therapeutic effective amount of a Varenicline is an amount that is a non-therapeutic amount when administer alone.

Aspects of the present specification can also be described as follows:

1. A method of treating a schizophrenic disorder by administering a combined therapy comprising one or more activators of an alpha-7 nicotinic acetylcholine receptor activity having 5-HT$_3$ receptor inhibitory activity and one or more activators of 5-HT$_3$ receptor activity.

2. The method of embodiment 1, wherein the one or more activators of an alpha-7 nicotinic acetylcholine receptor activity comprise one or more alpha-7 nicotinic acetylcholine receptor agonists, one or more positive allosteric modulators of an alpha-7 nicotinic acetylcholine receptor activity, or a combination thereof.

3. The method of embodiment 2, wherein the one or more alpha-7 nicotinic acetylcholine receptor agonists include an alpha-7 nicotinic acetylcholine receptor full agonist, an alpha-7 nicotinic acetylcholine receptor partial agonist, or an alpha-7 nicotinic acetylcholine receptor co-agonist.

4. The method of embodiment 2 or 3, wherein the one or more alpha-7 nicotinic acetylcholine receptor agonists include an alpha-7 nicotinic acetylcholine receptor pan agonist or an alpha-7 nicotinic acetylcholine receptor selective agonist.

5. The method of embodiment 2, wherein the one or more alpha-7 nicotinic acetylcholine receptor agonists include (+)-N-(1-azabicyclo[2.2.2]oct-3-yl)benzo[b] furan-2-carboxamide, A-582941, Acetylcholine, Amyloid beta, Anabasine, AR-R17779, Bradanicline, Choline, Encenicline, Epiboxidine, GTS-21, ICH-3, Nicotine, PHA-543,613, PHA-709829, PNU-282,987, SSR-180,711, TC-1698, Tilorone, Tropisetron, WAY-317,538, or any combination thereof.

6. The method of embodiment 2, wherein the one or more positive allosteric modulators of an alpha-7 nicotinic acetylcholine receptor activity include A-867744, AVL-3288, Galantamine, Ivermectin, Nefiracetam, NS-1738, PNU-120,596, or any combination thereof.

7. The method of any one of embodiments 1-6, wherein the 5-HT$_3$ receptor inhibitory activity comprise a 5-HT$_3$ receptor antagonistic activity, a 5-HT$_3$ receptor inverse agonistic activity, or a combination thereof.

8. The method of embodiment 7, wherein the 5-HT$_3$ receptor antagonistic activity is a 5-HT$_3$ receptor full antagonistic activity, a 5-HT$_3$ receptor partial antagonistic activity, or a 5-HT$_3$ receptor co-antagonistic activity.

9. The method of embodiment 7 or 8, wherein the 5-HT$_3$ receptor antagonistic activity is a 5-HT$_3$ receptor pan antagonistic activity or a 5-HT$_3$ receptor selective antagonistic activity.

10. The method of any one of embodiment 7-9, wherein the 5-HT$_3$ receptor antagonistic activity includes an antidepressant 5-HT$_3$ receptor antagonistic activity, an antiemetic 5-HT$_3$ receptor antagonistic activity, an antimalarial 5-HT$_3$ receptor antagonistic activity, an antipsychotic 5-HT$_3$ receptor antagonistic activity, a gastroprokinetic 5-HT$_3$ receptor antagonistic activity, or any combination thereof.

11. The method of embodiment 2, wherein the 5-HT$_3$ receptor inverse agonistic activity is a 5-HT$_3$ receptor full inverse agonistic activity, a 5-HT$_3$ receptor partial inverse agonistic activity, or a 5-HT$_3$ receptor co-inverse agonistic activity.

12. The method of embodiment 2 or 11, wherein the 5-HT$_3$ receptor inverse agonistic activity is a 5-HT$_3$ receptor pan inverse agonistic activity or a 5-HT$_3$ receptor selective inverse agonistic activity.

13. The method of any one of embodiments 1-12, wherein the one or more activators of 5-HT$_3$ receptor activity comprise one or more 5-HT$_3$ receptor agonists.

14. The method of embodiment 13, wherein the one or more 5-HT$_3$ receptor agonists include a 5-HT$_3$ receptor full agonist, a 5-HT$_3$ receptor partial agonist, a 5-HT$_3$ receptor co-agonist or a 5-HT$_3$ receptor super-agonist.

15. The method of embodiment 13 or 14, wherein the one or more 5-HT$_3$ receptor agonists include a 5-HT$_3$ receptor pan agonist or a 5-HT$_3$ receptor selective agonist.

16. The method of any one of embodiments 13-15, wherein the one or more 5-HT$_3$ receptor agonists have an alpha-7 nicotinic acetylcholine receptor agonistic activity.

17. The method of any one of embodiments 13-16, wherein the one or more 5-HT$_3$ receptor agonists include an alcohol having 5-HT$_3$ receptor agonist activity, meta-Chlorophenylbiguanide (1-(3-Chlorophenyl-biguanide)), Ibogaine, Phenylbiguanide, a piperazine having 5-HT$_3$ receptor agonist activity, RS-56812 (N-(1-Azabicyclo[2.2.2]octan-3-yl)-2-(1-methylindol-3-yl)-2-oxoacetamide), Serotonin, SR-57227 (1-(6-Chloropyridin-2-yl)piperidin-4-amine), SR-57227A (4-Amino-1-(6-chloro-2-pyridyl)-piperidine hydrochloride), a tryptamine having 5-HT$_3$ receptor agonist activity, Varenicline, a volatile gas having 5-HT$_3$ receptor agonist activity, and YM-31636 (2-(1H-imidazol-4-ylmethyl)-8H-indeno[1,2-d]thiazole).

18. The method of embodiment 17, wherein the alcohol having 5-HT$_3$ receptor agonist activity includes butanol, ethanol, or trichloroethanol.

19. The method of embodiment 17, wherein the piperazine having 5-HT$_3$ receptor agonist activity includes benzylpiperazine, meta-Chlorophenylpiperazine, or quipazine.

20. The method of embodiment 17, wherein the tryptamine having 5-HT$_3$ receptor agonist activity includes 2-methyl-5-hydroxytryptamine, α-Methyltryptamine, 5-carboxamidotryptamine, N,N-Dimethyl-5-hydroxytryptamine (Bufotenin), or 5-hydroxy-N,N,N-trimethyltryptammonium (bufotenine).

21. The method of embodiment 17, wherein the volatile gas having 5-HT$_3$ receptor agonist activity includes halothane, isoflurane, toluene, or trichloroethane.

22. The method of embodiment 1, wherein the one or more activators of an alpha-7 nicotinic acetylcholine receptor activity is Tropisetron and the one or more activators of 5-HT$_3$ receptor activity is Varenicline.

23. The method of any one of embodiments 2-4, and 13-16 wherein the one or more alpha-7 nicotinic acetylcholine receptor agonists is Tropisetron and the one or more 5-HT$_3$ receptor agonists is Varenicline.

24. The method of any one of embodiments 1-23, wherein the one or more activators of an alpha-7 nicotinic acetylcholine receptor activity and the one or more activators of 5-HT$_3$ receptor activity are provided in a therapeutic effective amount.

25. The method of any one of embodiments 2-23, wherein the one or more alpha-7 nicotinic acetylcholine receptor agonists, one or more positive allosteric modulators of an alpha-7 nicotinic acetylcholine receptor activity and/or the one or more 5-HT$_3$ receptor agonists are provided in a therapeutic effective amount.

26. The method of any one of embodiments 1-25, wherein the combination therapy comprises administration of a first composition comprising one or more activators of an alpha-7 nicotinic acetylcholine receptor activity and a second composition comprising one or more activators of 5-HT$_3$ receptor activity.

27. The method of any one of embodiments 1-25, wherein the combination therapy comprises administration of a single composition comprising one or more activators of an alpha-7 nicotinic acetylcholine receptor activity and one or more activators of 5-HT$_3$ receptor activity.

28. The method of any one of embodiments 2-25, wherein the combination therapy comprises administration of a first composition comprising one or more alpha-7 nicotinic acetylcholine receptor agonists and/or one or more positive allosteric modulators of an alpha-7 nicotinic acetylcholine receptor activity and a second composition comprising one or more 5-HT$_3$ receptor agonists.

29. The method of any one of embodiments 2-25, wherein the combination therapy comprises administration of a single composition comprising one or more alpha-7 nicotinic acetylcholine receptor agonists and/or one or more positive allosteric modulators of an alpha-7 nicotinic acetylcholine receptor activity and one or more 5-HT$_3$ receptor agonists.

30. A combined therapy comprising one or more activators of an alpha-7 nicotinic acetylcholine receptor activity having 5-HT$_3$ receptor inhibitory activity and one or more activators of 5-HT$_3$ receptor activity for use in treating a schizophrenic disorder.

31. The combined therapy of embodiment 30, wherein the one or more activators of an alpha-7 nicotinic acetylcholine receptor activity comprise one or more alpha-7 nicotinic acetylcholine receptor agonists, one or more positive allosteric modulators of an alpha-7 nicotinic acetylcholine receptor activity, or a combination thereof.

32. The combined therapy of embodiment 31, wherein the one or more alpha-7 nicotinic acetylcholine receptor agonists include an alpha-7 nicotinic acetylcholine receptor full agonist, an alpha-7 nicotinic acetylcholine receptor partial agonist, or an alpha-7 nicotinic acetylcholine receptor co-agonist.

33. The combined therapy of embodiment 31 or 32, wherein the one or more alpha-7 nicotinic acetylcholine receptor agonists includes an alpha-7 nicotinic acetylcholine receptor pan agonist or an alpha-7 nicotinic acetylcholine receptor selective agonist.

34. The combined therapy of embodiment 31, wherein the one or more alpha-7 nicotinic acetylcholine receptor agonists include (+)-N-(1-azabicyclo[2.2.2]oct-3-yl)benzo[b]furan-2-carboxamide, A-582941, Acetylcholine, Amyloid beta, Anabasine, AR-R17779, Bradanicline, Choline, Encenicline, Epiboxidine, GTS-21, ICH-3, Nicotine, PHA-543,613, PHA-709829, PNU-282,987, SSR-180,711, TC-1698, Tilorone, Tropisetron, WAY-317,538, or any combination thereof.

35. The combined therapy of embodiment 31, wherein the one or more positive allosteric modulators of an alpha-7 nicotinic acetylcholine receptor activity include A-867744, AVL-3288, Galantamine, Ivermectin, Nefiracetam, NS-1738, PNU-120,596, or any combination thereof.

36. The combined therapy of any one of embodiments 30-35, wherein the 5-HT$_3$ receptor inhibitory activity comprise a 5-HT$_3$ receptor antagonistic activity, a 5-HT$_3$ receptor inverse agonistic activity, or a combination thereof.

37. The combined therapy of embodiment 36, wherein the 5-HT$_3$ receptor antagonistic activity is a 5-HT$_3$ receptor full antagonistic activity, a 5-HT$_3$ receptor partial antagonistic activity, or a 5-HT$_3$ receptor co-antagonistic activity.

38. The combined therapy of embodiment 36 or 37, wherein the 5-HT$_3$ receptor antagonistic activity is a 5-HT$_3$ receptor pan antagonistic activity or a 5-HT$_3$ receptor selective antagonistic activity.

39. The combined therapy of any one of embodiment 36-38, wherein the 5-HT$_3$ receptor antagonistic activity includes an antidepressant 5-HT$_3$ receptor antagonistic activity, an antiemetic 5-HT$_3$ receptor antagonistic activity, an antimalarial 5-HT$_3$ receptor antagonistic activity, an antipsychotic 5-HT$_3$ receptor antagonistic activity, a gastroprokinetic 5-HT$_3$ receptor antagonistic activity, or any combination thereof.

40. The combined therapy of embodiment 30, wherein the 5-HT$_3$ receptor inverse agonistic activity is a 5-HT$_3$ receptor full inverse agonistic activity, a 5-HT$_3$ receptor partial inverse agonistic activity, or a 5-HT$_3$ receptor co-inverse agonistic activity.

41. The combined therapy of embodiment 30 or 40, wherein the 5-HT$_3$ receptor agonistic activity is a 5-HT$_3$ receptor pan inverse agonistic activity or a 5-HT$_3$ receptor selective inverse agonistic activity.

42. The combined therapy of any one of embodiments 30-41, wherein the one or more activators of 5-HT$_3$ receptor activity comprise one or more 5-HT$_3$ receptor agonists.

43. The combined therapy of embodiment 42, wherein the 5-HT₃ receptor agonist is a 5-HT₃ receptor full agonist, a 5-HT₃ receptor partial agonist, a 5-HT₃ receptor co-agonist or a 5-HT₃ receptor super-agonist.

44. The combined therapy of embodiment 42 or 43, wherein the 5-HT₃ receptor agonist is a 5-HT₃ receptor pan agonist or a 5-HT₃ receptor selective agonist.

45. The combined therapy of any one of embodiments 42-44, wherein the one or more 5-HT₃ receptor agonists have an alpha-7 nicotinic acetylcholine receptor agonistic activity.

46. The combined therapy of any one of embodiment 42-45, wherein the one or more 5-HT₃ receptor agonists is an alcohol having 5-HT₃ receptor agonist activity, meta-Chlorophenylbiguanide (1-(3-Chlorophenyl-biguanide)), Ibogaine, Phenylbiguanide, a piperazine having 5-HT₃ receptor agonist activity, RS-56812 (N-(1-Azabicyclo[2.2.2]octan-3-yl)-2-(1-methylindol-3-yl)-2-oxoacetamide), Serotonin, SR-57227 (1-(6-Chloropyridin-2-yl)piperidin-4-amine), SR-57227A (4-Amino-1-(6-chloro-2-pyridyl)-piperidine hydrochloride), a tryptamine having 5-HT₃ receptor agonist activity, Varenicline, a volatile gas having 5-HT₃ receptor agonist activity, and YM-31636 (2-(1H-imidazol-4-ylmethyl)-8H-indeno[1,2-d]thiazole).

47. The combined therapy of embodiment 46, wherein the alcohol having 5-HT₃ receptor agonist activity includes butanol, ethanol, or trichloroethanol.

48. The combined therapy of embodiment 46, wherein the piperazine having 5-HT₃ receptor agonist activity includes benzylpiperazine, meta-Chlorophenylpiperazine, or quipazine.

49. The combined therapy of embodiment 46, wherein the tryptamine having 5-HT₃ receptor agonist activity includes 2-methyl-5-hydroxytryptamine, α-Methyltryptamine, 5-carboxamidotryptamine, N,N-Dimethyl-5-hydroxytryptamine (Bufotenin), or 5-hydroxy-N,N,N-trimethyltryptammonium (bufotenidine).

50. The combined therapy of embodiment 46, wherein the volatile gas having 5-HT₃ receptor agonist activity includes halothane, isoflurane, toluene, or trichloroethane.

51. The combined therapy of embodiment 30, wherein the one or more activators of an alpha-7 nicotinic acetylcholine receptor activity is Tropisetron and the one or more activators of 5-HT₃ receptor activity is Varenicline.

52. The combined therapy of any one of embodiments 31-33 and 42-45 wherein the one or more alpha-7 nicotinic acetylcholine receptor agonists is Tropisetron and the one or more 5-HT₃ receptor agonists is Varenicline.

53. The combined therapy of any one of embodiments 30-52, wherein the one or more activators of an alpha-7 nicotinic acetylcholine receptor activity and the one or more activators of 5-HT₃ receptor activity are provided in a therapeutic effective amount.

54. The combined therapy of any one of embodiments 31-52, wherein the one or more alpha-7 nicotinic acetylcholine receptor agonists, one or more positive allosteric modulators of an alpha-7 nicotinic acetylcholine receptor activity, and/or the one or more 5-HT₃ receptor agonists are provided in a therapeutic effective amount.

55. The combined therapy of any one of embodiments 30-54, wherein the combination therapy comprises administration of a first composition comprising one or more activators of an alpha-7 nicotinic acetylcholine receptor activity and a second composition comprising one or more activators of 5-HT₃ receptor activity.

56. The combined therapy of any one of embodiments 30-54, wherein the combination therapy comprises administration of a single composition comprising one or more activators of an alpha-7 nicotinic acetylcholine receptor activity and one or more activators of 5-HT₃ receptor activity.

57. The combined therapy of any one of embodiments 31-54, wherein the combination therapy comprises administration of a first composition comprising one or more alpha-7 nicotinic acetylcholine receptor agonists and/or one or more positive allosteric modulators of an alpha-7 nicotinic acetylcholine receptor activity and a second composition comprising one or more 5-HT₃ receptor agonists.

58. The combined therapy of any one of embodiments 31-54, wherein the combination therapy comprises administration of a single composition comprising one or more alpha-7 nicotinic acetylcholine receptor agonists and/or one or more positive allosteric modulators of an alpha-7 nicotinic acetylcholine receptor activity, and one or more 5-HT₃ receptor agonists.

59. The method of any one of embodiments 1-29 or the combined therapy of any one of embodiments 30-58, wherein the schizophrenic disorder is a schizophrenia, a schizophreniform disorder, schizoaffective disorder, or a schizotypal personality disorder.

60. The method of embodiment 69 or the combined therapy of embodiment 69, wherein the schizophrenia is a disorganized schizophrenia, a catatonic schizophrenia, a paranoid schizophrenia, an undifferentiated schizophrenia, or a residual schizophrenia.

61. The method of embodiment 69 or the combined therapy of embodiment 69, wherein the schizophrenia is a ultra-high risk (UHR) or at risk mental state (ARMS) for psychosis, a first-episode psychosis, a chronic treatment responsive schizophrenia, a treatment resistant schizophrenia or a cognitive impaired schizophrenia.

62. A method of treating a schizophrenic disorder comprises, consists essentially of, or consists of administering a combined therapy comprising, consisting essentially of, or consisting of a therapeutically effective amount of Varenicline and a therapeutically effective amount of Tropisetron.

63. A method of treating a schizophrenia comprises, consists essentially of, or consists of administering a combined therapy comprising, consisting essentially of, or consisting of a therapeutically effective amount of Varenicline and a therapeutically effective amount of Tropisetron.

64. A method of treating a treatment resistant schizophrenia comprises, consists essentially of, or consists of administering a combined therapy comprising, consisting essentially of, or consisting of a therapeutically effective amount of Varenicline and a therapeutically effective amount of Tropisetron.

65. A method of treating a cognitive impaired schizophrenia comprises, consists essentially of, or consists of administering a combined therapy comprising, consisting essentially of, or consisting of a therapeutically effective amount of Varenicline and a therapeutically effective amount of Tropisetron.

66. A combined therapy comprising, consists essentially of, or consists of a therapeutically effective amount of Varenicline and a therapeutically effective amount of Tropisetron for use in treating a schizophrenic disorder.

67. A combined therapy comprising, consists essentially of, or consists of a therapeutically effective amount of Varenicline and a therapeutically effective amount of Tropisetron for use in treating a schizophrenia.

68. A combined therapy comprising, consists essentially of, or consists of a therapeutically effective amount of Varenicline and a therapeutically effective amount of Tropisetron for use in treating a treatment resistant schizophrenia.

69. A combined therapy comprising, consists essentially of, or consists of a therapeutically effective amount of Varenicline and a therapeutically effective amount of Tropisetron for use in treating a cognitive impaired schizophrenia.

EXAMPLES

The following non-limiting examples are provided for illustrative purposes only in order to facilitate a more complete understanding of representative embodiments now contemplated. These examples should not be construed to limit any of the embodiments described in the present specification, including those pertaining to the active agents, combination therapy, or methods or uses of treating a schizophrenic disorder disclosed herein.

Example 1

In Vivo Efficacy Study

This example shows the efficacy of a combination therapy comprising one or more activators of an alpha-7 nicotinic acetylcholine receptor activity having 5-HT$_3$ receptor inhibitory activity and one or more activators of 5-HT$_3$ receptor activity for use in treating a schizophrenic disorder.

Tropisetron is an alpha-7 nicotinic acetylcholine receptor activity having 5-HT$_3$ receptor inhibitory activity. As a potent anti-emetic, Tropisetron is used primarily in the treatment of patients with chemotherapy-induced or post-operative nausea and vomiting. With alpha-7 nicotinic acetylcholine receptors located in many brain areas important for cognition (including the hippocampus and frontal cortex), the alpha-7 nicotinic acetylcholine receptor activity of Tropisetron could potentially help modulate brain activity. Although some pro-cognitive effects in patients with schizophrenia have been seen, the therapeutic usefulness of Tropisetron in cognitive disorders is not feasible. First, Tropisetron is a peripheral, dose-response active ingredient since it is almost completely absorbed from the gastrointestinal tract. Second, Tropisetron is not suitable for chronic administration due to off-target gastrointestinal activity side effects that include a reduction in gut transit and constipation due to the 5-HT$_3$ receptor inhibitory activity of Tropisetron. Without wishing to be limited by any theory, the addition of, could substantially improve the tolerability of Tropisetron by off-setting peripheral side effects via stimulation of 5-HT3 in the GI tract. In addition, Varenicline itself has alpha-7 nicotinic acetylcholine receptor activity which can significantly enhance the therapeutic effect of Tropisetron. Thus, the combined administration of both these compounds would positively affect cognition whilst minimizing unwanted serotonergic-induced gastrointestinal side effects.

Normal male lister-hooded rats will be used to investigate latent inhibition based upon conditioned suppression of a lever press response for reward. Animals will initially undergo handling and habituation over a period of two-weeks followed by mild food restriction and initial training in the lever press response. Following 10 days lever training animals will be tested using a latent inhibition assay. This will be conducted over four consecutive days as follows: Day 1 will comprise conducting pre-exposure (PE) or control non pre-exposure (NPE) phases on animals; Day 2 will comprise conditioning animals using foot-shock conditioning regime (0.3 mA, 1 sec exposure); Day 3 will comprise re-baseline of animals; and Day 4 will comprise conducting a test phase on animals.

An amphetamine induced latent inhibition study will then be performed. A preclinical latent inhibition assay will be conducted as described in U.S. Provisional Patent Application Ser. No. 62/820,490, filed on Mar. 19, 2019 and titled "Method and Uses of Diagnosing and Recommending Treatment for a Psychotic Disorder", which is hereby incorporated by reference in its entirety, except that the assay will be modified for animal assessment as discussed herein. In this study, control (NPE) animals will be compared to animals pre-exposed to the foot-shock conditioning cue following vehicle or amphetamine treatment (n=8 per group, 4 groups). This study will confirm the dose of amphetamine required to induce an optimal latent inhibition effect for subsequent testing in combination with the novel compounds.

Following an amphetamine induced latent inhibition study, a dose-response study using an alpha-7 nicotinic acetylcholine receptor activity having 5-HT$_3$ receptor inhibitory activity or 5-HT$_3$ receptor agonist will be performed. This 12-week study will test the ability of a single agent to attenuate an amphetamine-induced deficit in latent inhibition. Each active agent will be evaluated at three doses based on current pharmacokinetic and clinical data and compared to vehicle control. Each active agent test group will be divided into four treatment groups (n=12) as follows: 1) alpha-7 nicotinic acetylcholine receptor activity having 5-HT$_3$ receptor inhibitory activity treated group comprising placebo/placebo animals; placebo/Tropisetron dose 1 animals; placebo/Tropisetron dose 2 animals; placebo/Tropisetron dose 3 animals; and 2) 5-HT$_3$ receptor agonist treated group comprise placebo/placebo animals; placebo/varenicline dose 1 animals; placebo/varenicline dose 2 animals; placebo/varenicline dose 3 animals.

Following a dose-response study, a combination therapy study will be performed using the optimal therapeutically effective amount of an alpha-7 nicotinic acetylcholine receptor activity having 5-HT$_3$ receptor inhibitory activity and 5-HT$_3$ receptor agonist as determined in a dose-response study. This 6-week study will demonstrate the efficacy of a combination therapy using an alpha-7 nicotinic acetylcholine receptor activity having 5-HT$_3$ receptor inhibitory activity and 5-HT$_3$ receptor agonist compared to either active agent alone. Each treatment group (n=12) will be tested at a single dose in amphetamine-treated animals and compared to an amphetamine plus vehicle treated group (n=12) as follows: 1) alpha-7 nicotinic acetylcholine receptor activity having 5-HT$_3$ receptor inhibitory activity alone treated group comprising animals treated with a single optimal effective therapeutic amount of Tropisetron; 2) 5-HT$_3$ receptor agonist alone treated group comprising animals treated with a single optimal effective therapeutic amount of Varenicline; 3) combination therapy treated group comprising animals treated with a single optimal effective therapeutic amount of both Tropisetron and Varenicline; and 4) control group comprising animals treated with Amphetamine and vehicle.

Example 2

In Vivo Efficacy Study

This example shows the efficacy of a combination therapy comprising one or more activators of an alpha-7 nicotinic acetylcholine receptor activity having 5-HT$_3$ receptor inhibitory activity and one or more activators of 5-HT$_3$ receptor activity for use in treating a schizophrenic disorder.

C57BL/6 mice will be used to investigate latent inhibition (LI) conditioned emotional response cessation of drinking model in mice as described in, e.g., Bay-Richter, et al., *Enhanced Latent Inhibition in Dopamine Receptor-Deficient Mice is Sex-Specific for the D1 but not D2 Receptor Subtype: Implications for Antipsychotic Drug Action*, Int. J. Neuropsychopharmacol. 12(3): 403-414 (2009); Bay-Richter, et al., *D-Amphetamine and Antipsychotic Drug Effects on Latent Inhibition in Mice Lacking Dopamine D2 Receptors*, Neuropsychopharmacology 38(8): 1512-1520 (2013); O'Callaghan, et al., *Potentiation of Latent Inhibition by Haloperidol and Clozapine is Attenuated in Dopamine D2 Receptor (Drd-2)-Deficient Mice: Do Antipsychotics Influence Learning to Ignore Irrelevant Stimuli via Both Drd-2 and Non-Drd-2 Mechanisms?*, J. Psychopharmacol. 28(10): 973-977 (2014), each of which are hereby incorporated by reference in its entirety. Animals will initially undergo handling and habituation over a period of one-week where mice will be water restricted for 23 hours per day with one-hour free access to water. On Day 1 to Day 6, animals will undergo lick training where mice will have access to water in a chamber for 15 minutes and the number of licks per animal will be recorded. On Day 7 (pre-exposure) mice will be placed in a testing chamber with access to water withdrawn. One group will receive 20 presentations [determined from prior experiments to produce reduced LI in controls] of a 5 second 85 dB tone with a 15 second inter-stimulus interval (pre-exposed group, PE); a control group of non-pre-exposed (NPE) mice will be placed in a testing chamber with access to water withdrawn for an identical period of time but will not receive a tone pre-exposure. On Day 8 (conditioning) mice will be placed in a testing chamber with access to water withdrawn. After two minutes, two tone-footshock pairings will be presented. Tones are of 5 second duration and followed by a 1 second 0.38 mA footshock with an inter-trial-interval of 2.5 minutes. Mice will remain in the chamber for 2.5 minutes following the second shock presentation. On Day 16-17 (re-baseline) mice will be placed in a testing chamber for 15 minute and given free access to water to re-establish stable licking, criterion will be that mice that did not complete more than 300 licks continuously will not continue to the test stage. On Day 18 (Test) mice will be placed in a testing chamber with free access to water. Number of licks for each animal will be recorded and time taken to complete 80-90 licks (A) and 90-100 licks (B) recorded. After completion of 90 licks, a 5 second 85 dB tone will be presented until an animal reaches 100 licks or 600 seconds had elapsed. A suppression ratio (SR) will be calculated according to the formula A/(A+B) yielding a scale of 0 to 0.5. Low SR indicates increased suppression of drinking; high SR indicates decreased suppression of drinking. LI is seen as higher SR in PE versus NPE groups.

In one series of experiments, procognitive doses of Tropisetron and Varenicline will be established using a standard latent inhibition test of attention (as described above) in mice. Animals will be divided into eight groups of 15 animals each (120 total mice), and two series of experiments of 60 animals per experiment will be conducted. In the first experimental series, the effects of Tropisetron on latent inhibition will be assessed at three different doses (Table 1). In the second experimental series the effects of Varenicline on latent inhibition will be assessed at three different doses (Table 2). The results of these experiments will establish procognitive doses of Tropisetron and Varenicline that will potentiate low levels of latent inhibition. These results will also enable the identification of suboptimal doses of Tropisetron and/or Varenicline. Gut motility will also be evaluated for safety purposes.

TABLE 1

| Experimental Series 1 | | | |
|---|---|---|---|
| Non-Preexposed (NPE) | | Pre-Exposed (PE) | |
| Group 1 | Vehicle = placebo | Group 5 | Vehicle = placebo |
| Group 2 | Dose 1 Tropisetron | Group 6 | Dose 1 Tropisetron |
| Group 3 | Dose 2 Tropisteron | Group 7 | Dose 2 Tropisetron |
| Group 4 | Dose 3 Tropisteron | Group 8 | Dose 3 Tropistron |

TABLE 2

| Experimental Series 2 | | | |
|---|---|---|---|
| Non-Preexposed (NPE) | | Pre-Exposed (PE) | |
| Group 1 | Vehicle = Placebo | Group 5 | Vehicle = Placebo |
| Group 2 | Dose 1 Varenicline | Group 6 | Dose 1 Varenicline |
| Group 3 | Dose 2 Varenicline | Group 7 | Dose 2 Varenicline |
| Group 4 | Dose 3 Varenicline | Group 8 | Dose 3 Varenicline |

In a third series of experiments, a combined Tropisetron and Varenicline treatment that potentiates the procognitive effects in latent inhibition will be determined. Animals will be divided into eight groups of 15 animals each (120 total mice), and two series of experiments of 60 animals will be conducted using the 18-day latent inhibition protocol discussed above. In both experimental series the effects of Tropisetron alone, Varenicline alone and a combined Tropisetron and Varenicline treatment on latent inhibition will be assessed (Table 3). The results of these experiments will establish that a combined Tropisetron and Varenicline treatment with each drug will potentiate the pro-cognitive effects in latent inhibition, compared to either drug administered alone. Gut motility will also be evaluated for safety purposes.

TABLE 3

| Experimental Series 3 | | | |
|---|---|---|---|
| Non-Preexposed (NPE) | | Pre-Exposed (PE) | |
| Group 1 | Vehicle = placebo | Group 5 | Vehicle = placebo |
| Group 2 | Tropisetron | Group 6 | Tropisetron |
| Group 3 | Varenicline | Group 7 | Varenicline |
| Group 4 | Tropisteron + Varenicline | Group 8 | Tropisteron + Varenicline |

In a fourth series of experiments, a reversal of D-amphetamine induced disruption of latent inhibition using a combined Tropisetron and Varenicline treatment will be assessed. Animals will be divided into ten groups of 15 animals each (150 total mice), and two series of experiments of 72 animals will be conducted using the 18-day latent inhibition protocol discussed above. In both experimental series the effects of Tropisetron alone, Varenicline alone and a combined Tropisetron and Varenicline treatment, in the presence of D-amphetamine, on latent inhibition will be assessed (Table 4). The results of these experiments will establish that a combined Tropisetron and Varenicline treatment reverses D-amphetamine induced disruption of latent inhibition. Gut motility will also be evaluated for safety purposes.

TABLE 4

| Experimental Series 4 | | | |
| --- | --- | --- | --- |
| Non-Preexposed (NPE) | | Pre-Exposed (PE) | |
| Group 1 | Vehicle = placebo | Group 6 | Vehicle = placebo |
| Group 2 | D-amphetamine | Group 7 | D-amphetamine |
| Group 3 | D-amphetamine + Tropisteron + Varenicline | Group 8 | D-amphetamine + Tropisteron + Varenicline |
| Group 4 | Tropisetron | Group 9 | Tropisetron |
| Group 5 | Varenicline | Group 10 | Varenicline |

In a fifth series of experiments, the optimal dose of MK801 that is able to produce abnormally persistent latent inhibition will be assessed. Animals will be divided into eight groups of 15 animals each (120 total mice), and the latent inhibition protocol discussed above will be used, except that there will be 4 tone-shock pairings administered to produce low LI (to then be reversed and potentiated by MK801). The effects of MK801 on latent inhibition will be assessed at two different doses and in the presence of Clozapine (Table 5). The results of experiment 5 will establish the optimal dose of MK801 that is able to produce abnormally persistent latent inhibition before moving onto experiment 6.

TABLE 5

| Experimental Series 5 | | | |
| --- | --- | --- | --- |
| Non-Preexposed (NPE) | | Pre-Exposed (PE) | |
| Group 1 | Vehicle = placebo | Group 5 | Vehicle = placebo |
| Group 2 | Dose 1 MK801 | Group 6 | Dose 1 MK801 |
| Group 3 | Dose 2 MK801 | Group 7 | Dose 2 MK801 |
| Group 4 | MK801 + Clozapine | Group 8 | MK801 + Clozapine |

In a sixth series of experiments, the ability of the combined Tropisetron and Varenicline treatment to reverse the MK801 induced abnormally persistent latent inhibition effect will be assessed. Animals will be divided into ten groups of 15 animals each (150 total mice), and the latent inhibition protocol discussed above will be used, as per experiment 5 with 4 tone-shock pairings administered to produce low LI. The effects of Tropisteron alone, Varenicline alone and a combined Tropisetron and Varenicline treatment in the presence of MK801 on latent inhibition will be assessed (Table 6). The results of this experiment will establish that a combined Tropisetron and Varenicline treatment reverses an MK801 induced abnormally persistent effect of latent inhibition. Gut motility will also be evaluated for safety purposes.

TABLE 6

| Experimental Series 6 | | | |
| --- | --- | --- | --- |
| Non-Preexposed (NPE) | | Pre-Exposed (PE) | |
| Group 1 | Vehicle = placebo | Group 6 | Vehicle = placebo |
| Group 2 | MK801 | Group 7 | MK801 |
| Group 3 | MK801 + Tropisteron + Varenicline | Group 8 | MK801 + Tropisteron + Varenicline |

TABLE 6-continued

| Experimental Series 6 | | | |
| --- | --- | --- | --- |
| Non-Preexposed (NPE) | | Pre-Exposed (PE) | |
| Group 4 | Tropisetron | Group 9 | Tropisetron |
| Group 5 | Varenicline | Group 10 | Varenicline |

In closing, it is to be understood that, although aspects of the present specification are highlighted by referring to specific embodiments, one skilled in the art will readily appreciate that these described embodiments are only illustrative of the principles of the subject matter disclosed herein. The specific embodiments are not intended to be exhaustive or to limit the invention to the precise forms disclosed. Therefore, it should be understood that the disclosed subject matter is in no way limited to a particular compound, composition, article, apparatus, methodology, protocol, and/or reagent, etc., described herein, unless expressly stated as such. In addition, those of ordinary skill in the art will recognize that certain changes, modifications, permutations, alterations, additions, subtractions and sub-combinations thereof can be made in accordance with the teachings herein without departing from the spirit of the present specification. It is therefore intended that the scope of the invention is not to be limited by this detailed description. Furthermore, it is intended that the following appended claims and claims hereafter introduced are interpreted to include all such changes, modifications, permutations, alterations, additions, subtractions and sub-combinations as are within their true spirit and scope.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified, thus fulfilling the written description of all Markush groups used in the appended claims.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. For instance, as mass spectrometry instruments can vary slightly in determining the mass of a given analyte, the term "about" in the context of the mass of an ion or the mass/charge ratio of an ion refers to $+/-0.50$ atomic mass unit. At the very least, and not as an attempt to limit the application of the doctrine of equivalents to the scope of the claims, each numerical indication should at least be construed in light of the number of reported significant digits and by applying ordinary rounding techniques.

Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as, e.g., "first," "second," "third," etc. —for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising", variations thereof such as, e.g., "comprise" and "comprises", and equivalent open-ended transitional phrases thereof like "including," "containing" and "having", encompass all the expressly recited elements, limitations, steps, integers, and/or features alone or in combination with unrecited subject matter; the named elements, limitations, steps, integers, and/or features are essential, but other unnamed elements, limitations, steps, integers, and/or features may be added and still form a construct within the scope of the claim. Specific embodiments disclosed herein may be further limited in the claims using the closed-ended transitional phrases "consisting of" or "consisting essentially of" (or variations thereof such as, e.g., "consist of", "consists of", "consist essentially of", and "consists essentially of") in lieu of or as an amendment for "comprising." When used in the claims, whether as filed or added per amendment, the closed-ended transitional phrase "consisting of" excludes any element, limitation, step, integer, or feature not expressly recited in the claims. The closed-ended transitional phrase "consisting essentially of" limits the scope of a claim to the expressly recited elements, limitations, steps, integers, and/or features and any other elements, limitations, steps, integers, and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps, integers, and/or features specifically recited in the claim, whereas the meaning of the closed-ended transitional phrase "consisting essentially of" is being defined as only including those elements, limitations, steps, integers, and/or features specifically recited in the claim and those elements, limitations, steps, integers, and/or features that do not materially affect the basic and novel characteristic(s) of the claimed subject matter. Therefore, the open-ended transitional phrase "comprising" (and equivalent open-ended transitional phrases thereof) includes within its meaning, as a limiting case, claimed subject matter specified by the closed-ended transitional phrases "consisting of" or "consisting essentially of." As such, the embodiments described herein or so claimed with the phrase "comprising" expressly and unambiguously provide description, enablement, and support for the phrases "consisting essentially of" and "consisting of."

All patents, patent publications, and other references cited and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard is or should be construed as an admission that the inventors are not entitled to antedate such disclosure by virtue of prior invention or for any other reason. All statements as to the date or representation as to the contents of these documents are based on the information available to the applicant and do not constitute any admission as to the correctness of the dates or contents of these documents.

Lastly, the terminology used herein is for the purpose of describing particular embodiments only and is not intended to limit the scope of the present invention, which is defined solely by the claims. Accordingly, the present invention is not limited to that precisely as shown and described.

The invention claimed is:

1. A method of treating a schizophrenic disorder by administering a combination therapy comprising Tropisetron and Varenicline.

2. The method of claim 1, wherein the Tropisetron and Varenicline are provided in a therapeutically effective amount.

3. The method of claim 2, wherein the therapeutically effective amount of Tropisetron and Varenicline is one where the amount of Tropisetron is a suboptimal therapeutic amount when administered alone and the amount of Varenicline is a suboptimal therapeutic amount when administered alone.

4. The method of claim 1, wherein the combination therapy comprises administration of a first composition comprising Tropisetron and a second composition comprising Varenicline.

5. The method of claim 1, wherein the combination therapy comprises administration of a single composition comprising Tropisetron and Varenicline.

6. The method of claim 2, wherein the therapeutically effective amount is between about 2 mg to about 75 mg of Tropisetron and between about 0.25 mg to about 4 mg of Varenicline.

7. The method of claim 2, wherein the therapeutically effective amount is between about 5 mg to about 50 mg of Tropisetron and between about 0.5 mg to about 2 mg of Varenicline.

8. The method of claim 2, wherein the therapeutically effective amount is between about 2 mg to about 50 mg of Tropisetron and between about 0.5 mg to about 4 mg of Varenicline.

9. The method of claim 3, where the suboptimal therapeutic amount is less than 80%, less than 75%, less than 70%, less than 60%, less than 55%, or less than 50% of an optimal therapeutic effective amount of Tropisetron or Varenicline.

10. The method of claim 1, wherein the schizophrenic disorder is a schizophrenia, a schizophreniform disorder, a schizoaffective disorder, or a schizotypal personality disorder.

11. The method of claim 10, wherein the schizophrenia is a disorganized schizophrenia, a catatonic schizophrenia, a paranoid schizophrenia, an undifferentiated schizophrenia, or a residual schizophrenia.

12. The method of claim 10, wherein the schizophrenia is an ultra-high risk (UHR) or at risk mental state (ARMS) for psychosis, a first-episode psychosis, a chronic treatment responsive schizophrenia, a treatment resistant schizophrenia, or a cognitive impaired schizophrenia.

13. The method of claim 2, wherein the schizophrenic disorder is schizophrenia, and the therapeutically effective amount is between about 2 mg to about 75 mg of Tropisetron and between about 0.25 mg to about 4 mg of Varenicline.

14. The method of claim 2, wherein the schizophrenic disorder is treatment resistant schizophrenia, and the therapeutic effective amount is between about 2 mg to about 75 mg of Tropisetron and between about 0.25 mg to about 4 mg of Varenicline.

15. The method of claim 2, wherein the schizophrenic disorder is a cognitive impaired schizophrenia, and the therapeutic effective amount is between about 2 mg to about 75 mg of Tropisetron and between about 0.25 mg to about 4 mg of Varenicline.

16. The method of claim 13, wherein the therapeutic effective amount is between about 2 mg to about 50 mg of Tropisetron and between about 0.5 mg to about 4 mg of Varenicline.

17. The method of claim 13, wherein therapeutic effective amount is between about 5 mg to about 50 mg of Tropisetron and about 0.5 mg to about 2 mg of Varenicline.

18. The method of claim 14, wherein the therapeutic effective amount is between about 2 mg to about 50 mg of Tropisetron and between about 0.5 mg to about 4 mg of Varenicline.

19. The method of claim 14, wherein therapeutic effective amount is between about 5 mg to about 50 mg of Tropisetron and about 0.5 mg to about 2 mg of Varenicline.

20. The method of claim 15, wherein the therapeutic effective amount is between about 2 mg to about 50 mg of Tropisetron and between about 0.5 mg to about 4 mg of Varenicline.

21. The method of claim 15, wherein therapeutic effective amount is between about 5 mg to about 50 mg of Tropisetron and about 0.5 mg to about 2 mg of Varenicline.

* * * * *